United States Patent [19]

Manes

[11] Patent Number: 4,574,801
[45] Date of Patent: Mar. 11, 1986

[54] ELECTROSURGICAL UNIT WITH REGULATED OUTPUT

[75] Inventor: Michael R. Manes, Littleton, Colo.

[73] Assignee: Aspen Laboratories, Inc., Englewood, Colo.

[21] Appl. No.: 584,954

[22] Filed: Feb. 29, 1984

[51] Int. Cl.⁴ .............................................. A61B 17/39
[52] U.S. Cl. ......................... 128/303.14; 128/303.17; 330/59; 331/186
[58] Field of Search ........................ 128/303.13–303.18; 330/59, 297; 331/186

[56] References Cited

U.S. PATENT DOCUMENTS

| | | | |
|---|---|---|---|
| 3,471,700 | 10/1969 | Presti | 330/59 X |
| 3,801,800 | 4/1974 | Newton | 307/117 |
| 3,812,858 | 5/1974 | Oringer | 128/303.14 |
| 3,875,945 | 4/1975 | Friedman | 128/303.14 |
| 3,923,063 | 12/1975 | Andrews et al. | 128/303.14 |
| 3,963,030 | 6/1976 | Newton | 128/303.14 |
| 3,964,487 | 6/1976 | Judson | 128/303.14 |
| 4,024,467 | 5/1977 | Andrews et al. | 332/14 |
| 4,030,501 | 6/1977 | Archibald | 128/303.14 |
| 4,092,986 | 6/1978 | Schneiderman | 128/303.14 |
| 4,126,137 | 11/1978 | Archibald | 128/303.14 |
| 4,191,188 | 3/1980 | Belt | 128/303.13 |
| 4,343,310 | 8/1982 | DuBose et al. | 128/303.14 |
| 4,438,766 | 3/1984 | Bowers | 128/303.14 |

*Primary Examiner*—Lee S. Cohen
*Attorney, Agent, or Firm*—Paul David Schoenle

[57] ABSTRACT

An electrosurgical unit having feedforward power regulation. In one embodiment there is an amplifier which produces a pulse modulated electrosurgical output signal. A microprocessor calculates an adjusted pulse width (duty cycle) just sufficient to account for the power changes due to voltage fluctuations. The microprocessor controls the pulse width of the gate voltage of a power transistor in the amplifier to regulate the amplifier output. In another embodiment the supply voltage is fed into the base drive circuitry of an amplifier power transistor through the photo-resistor side of an optoisolator. The lamp brightness of the optoisolator and thus the gain of the base drive circuitry is adjusted by the amplifier power level control. The nonlinearity of the optoisolator complements the nonlinearity of the amplifier so that the net gain in the amplifier drive at any power setting is just sufficient to account for the voltage fluctuation.

5 Claims, 21 Drawing Figures

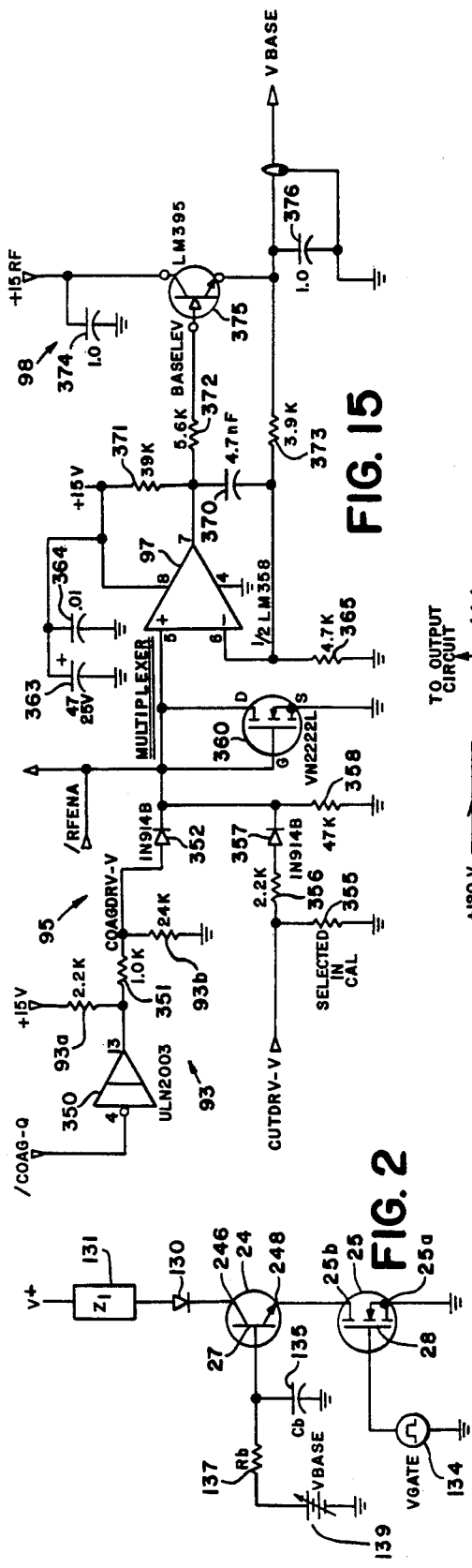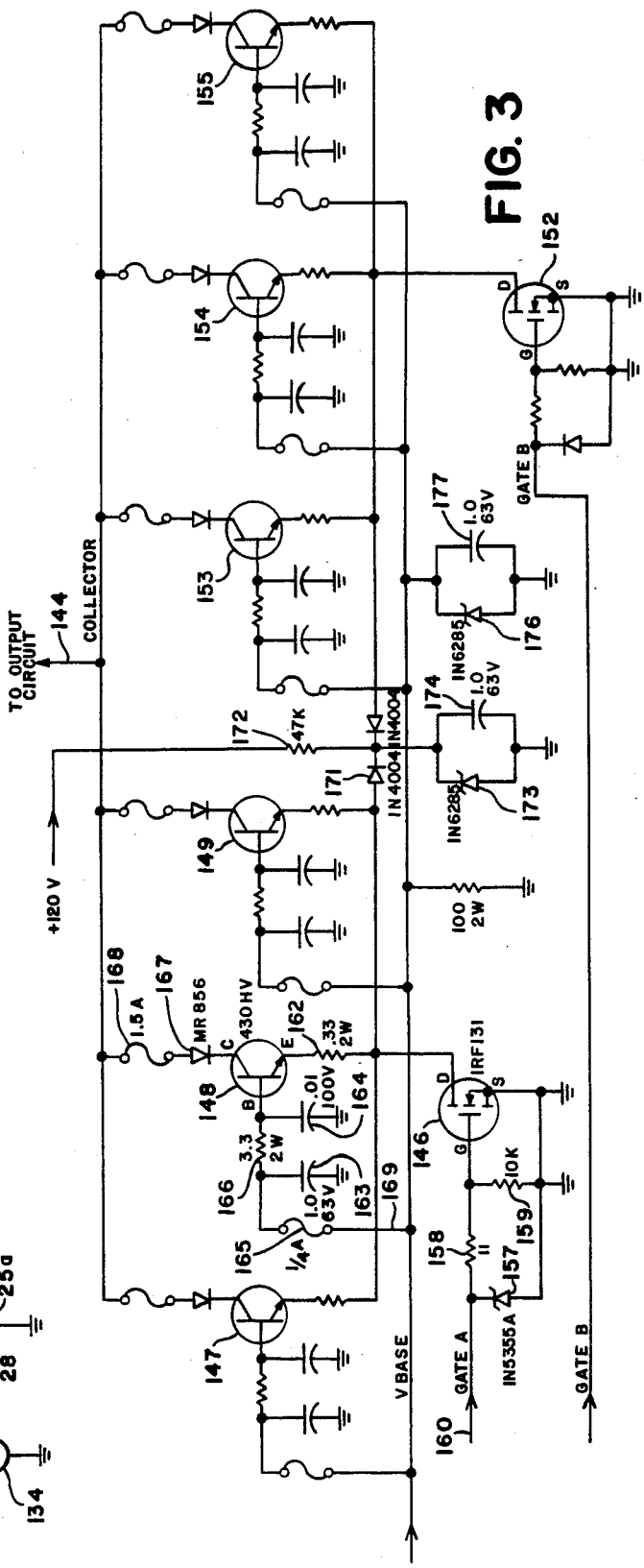

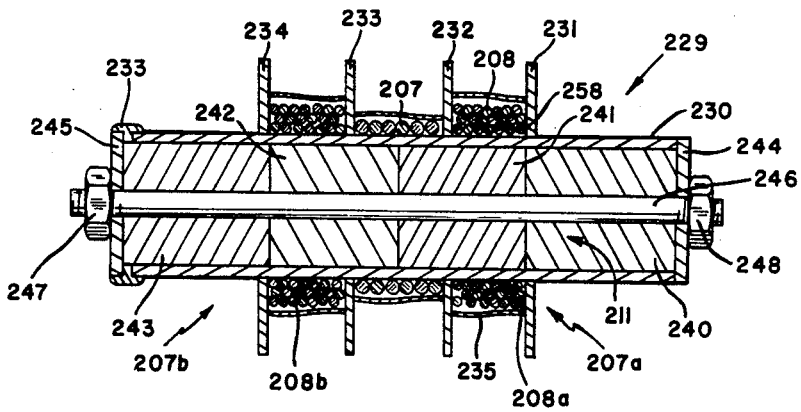
FIG. 8
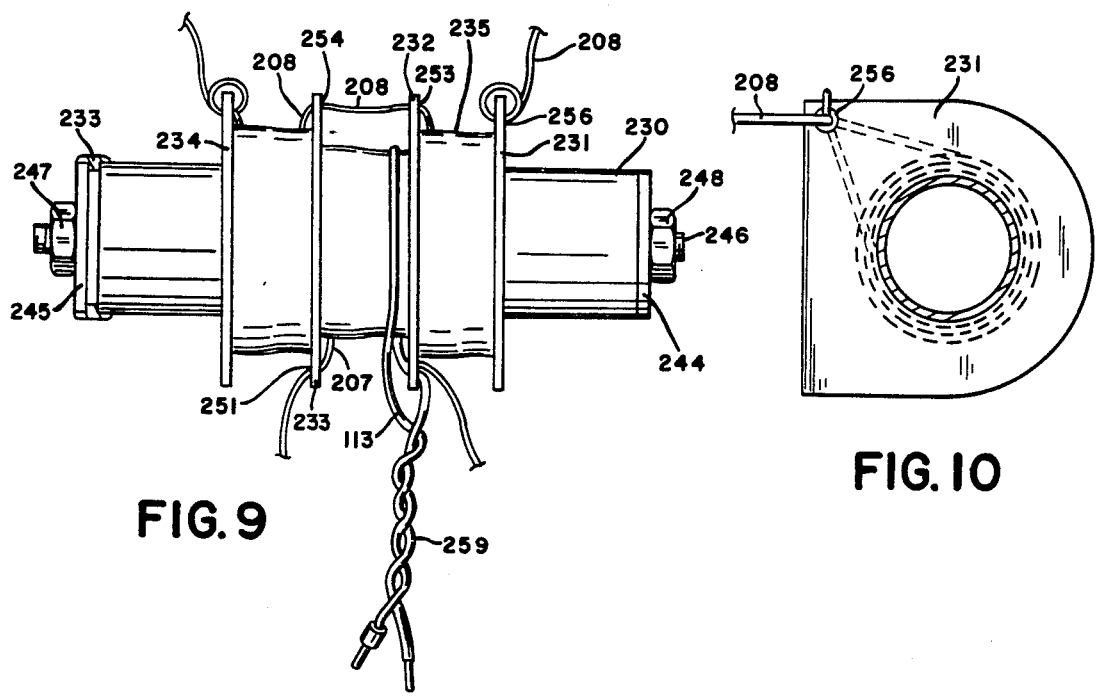
FIG. 9
FIG. 10

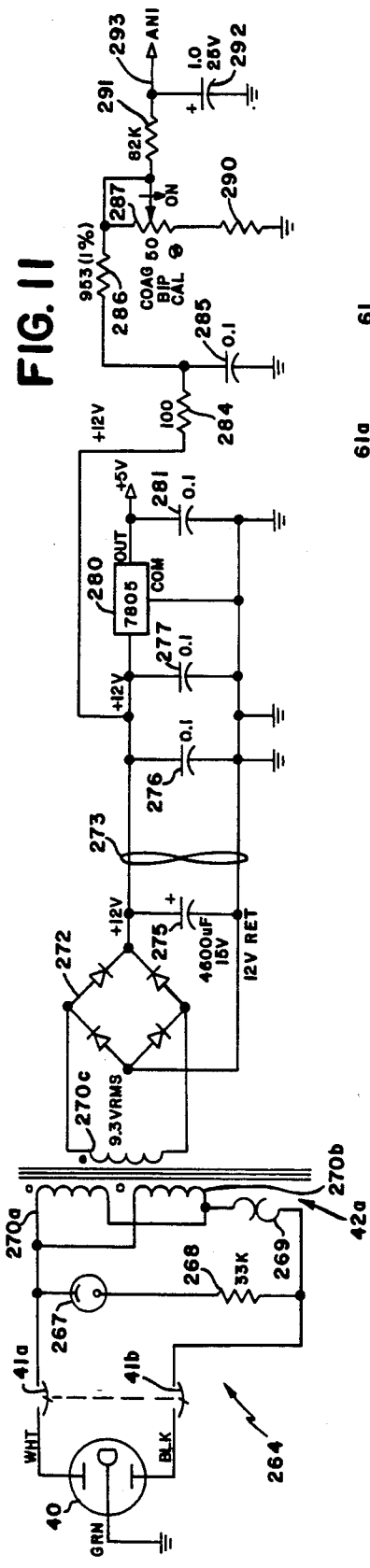
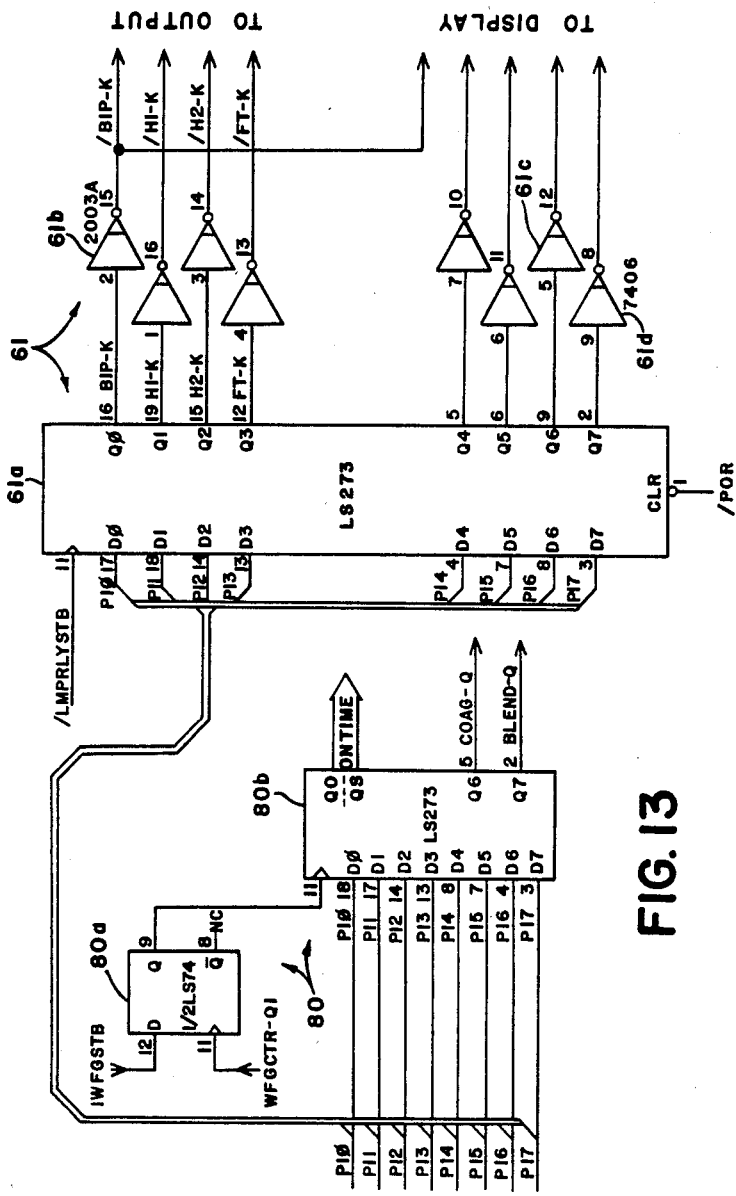
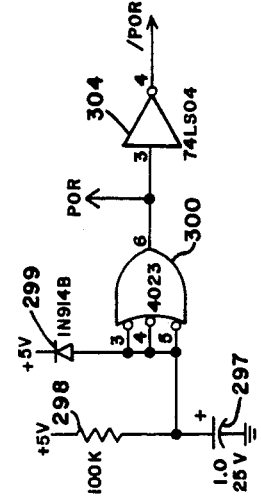
FIG. 11
FIG. 12
FIG. 13

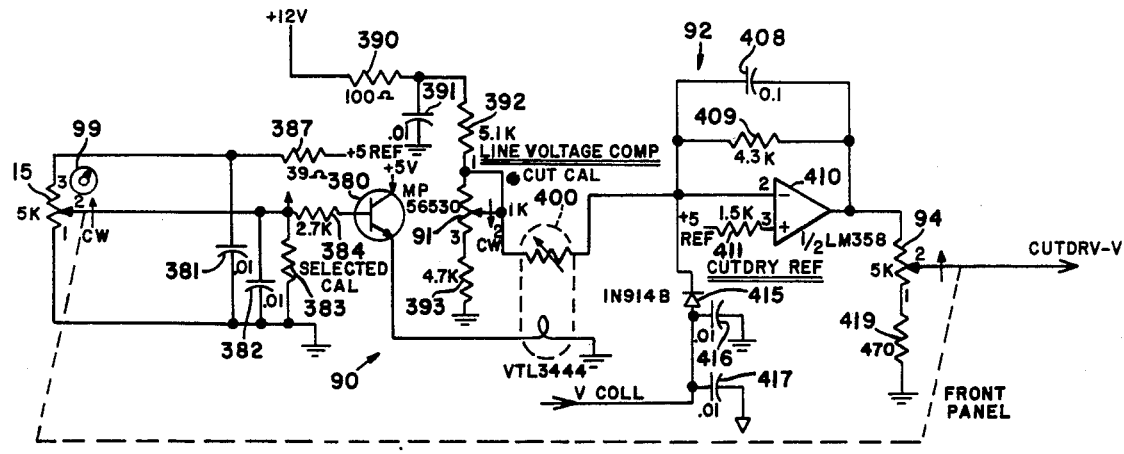
FIG. 16
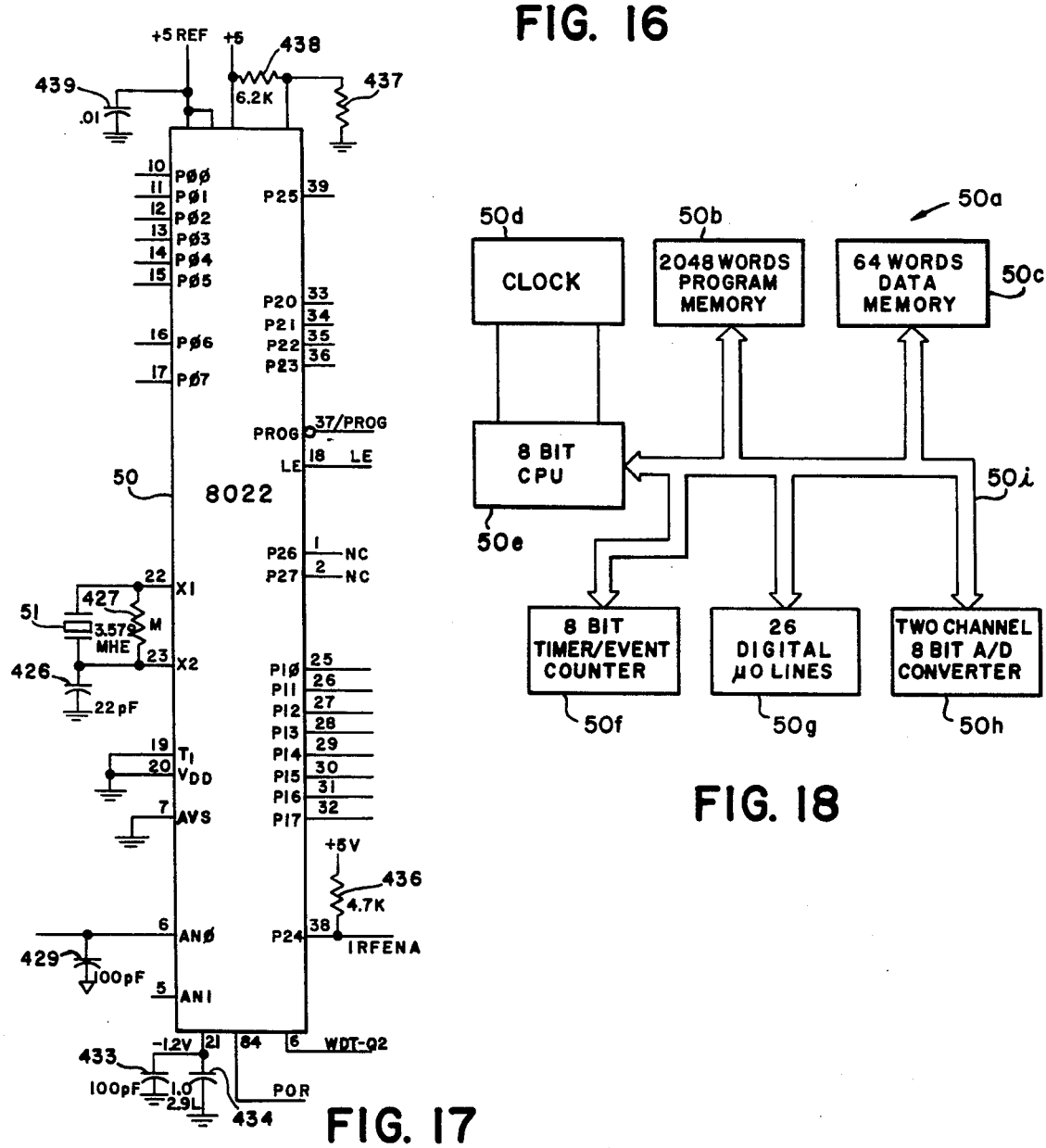
FIG. 17
FIG. 18

ELECTROSURGICAL UNIT WITH REGULATED OUTPUT

BACKGROUND OF THE INVENTION

1. Field of the Invention

The invention in general relates to electrosurgery, and in particular to an electrosurgical unit having a regulated power output.

2. Description of the Prior Art

Electrosurgical generators which produce high frequency electric currents used for cutting of tissue and coagulation of small blood vessels have been well-known for several generations. Since the amount of cutting or coagulation performed is related to the voltage and power output of the generator, it is also known that it is desirable that the output signal of the generator be regulated. By a regulated output signal it is meant that the signal is controlled so that the fluctuations in the line input voltage do not substantially affect the power output. By substantially, it is meant that the output voltage is sufficiently regulated so that differences in cutting or coagulation are not noticable by the surgeon for normal fluctuation levels within conventional AC voltage lines.

The most common manner of obtaining a regulated output is through the use of regulated power supplies. U.S. Pat. No. 3,963,030 issued David W. Newton, discloses a feedback circuit for regulating the output of an electrosurgical generator. This feedback circuit includes a current sensor which senses the current and the output circuitry and a comparator which compares the output voltage to a reference voltage and which then adjusts the amplifier to account for variations in the amplified signal. Since fluctuations in the amplified signal are proportional to the fluctuations of the supply voltage, this method provides the desired regulation. See also U.S. Pat. No. 4,092,986 issued to Max Schneiderman.

The prior art means for regulating the output of an electrosurgical unit have several disadvantages. A regulated power supply is relatively expensive, bulky, consumes significant electrical energy and produces significant heat. These disadvantages are especially accented when a high output supply, such as the supply used for the power output stages of an electrosurgical generator, are regulated. Since under actual use the output of an electrosurgical unit varies with changing conditions at or between its electrodes, any easily measured output parameter will also vary. For example, the voltage will change with the change in resistance between the electrodes. Thus such output parameters are not generally indicative of the variations in line voltage. As a result the feedback type of circuitry is not as reliable and effective as a feedforward compensated power supply. Moreover, oscillations can occur in output parameters that are controlled by feedback loops.

SUMMARY OF THE INVENTION

It is an object of the present invention to provide an electrosurgical generator having a regulated power output that is simpler and more efficient than prior art regulated electrosurgical generators.

It is a further object of the invention to provide an electrosurgical unit that utilizes feedforward circuitry. By feedforward circuitry, it is meant that the voltage fluctuations within the electrosurgical unit are sensed or sampled at a point in the circuitry of the electrosurgical generator that is before (with respect to the direction of current flow) the point at which the power is regulated.

It is a further object of the present invention to provide an electrosurgical generator which meets one or more of the above objects and in which the electrical components that provide the regulation are also components of the amplifier; that is, the amplifier components perform double duty, thus making the design less expensive and simpler.

It is a further object of the invention to provide one or more of the above objects in an electrosurgical unit in which the regulating circuitry accounts for any non-linearity in the amplifier.

It is another object of the invention to provide one or more of the above objects in an electrosurgical unit in which a digital microprocessor controls the electrosurgical output signal.

It is yet another object of the invention to provide a power regulated electrosurgical unit in which the regulation circuitry consumes a minimum amount of electrical energy, thus reducing the heat generated by the system and making the system more acceptable in the surgical environment.

The invention provides an electrosurgical unit comprising a power source, a feedforward means responsive to voltage fluctuations at the power source for producing a regulation signal, and an amplifier means responsive to the regulation signal for producing an electrosurgical output signal that is substantially independent of the voltage fluctuations of the power source. Preferably the feedforward means includes an optoisolator. In another aspect of the invention, preferably the feedforward means includes a microprocessor. In one preferred embodiment of the invention the amplifier means includes a means for pulse modulating the electrosurgical output signal and the feedforward means comprises a means for providing a signal for regulating the duty cycle of the modulated output. In another preferred embodiment of the invention, the feedforward means comprises a means for storing a predetermined signal representative of a desired voltage, and a means responsive to the voltage fluctuations of the source and to the predetermined signal for producing the regulation signal.

In another aspect of the invention, the invention provides an electrosurgical unit comprising a power source, an amplifier means electrically connected to the power source for producing an electrosurgical output signal, and a means for regulating the output signal comprising a means for storing a predetermined signal representative of a desired output signal, and a means responsive to the predetermined signal and to the voltage fluctuations of the power source for regulating the output signal.

In a further aspect of the invention, the invention provides an electrosurgical unit comprising a power source, an amplifier means electrically connected to the power source for producing and electrosurgical output signal, the amplifier including a means for regulating the output signal which includes a means for adjusting for non-linearities in the amplifier. Preferably the means for adjusting includes an optoisolator.

In yet another aspect, the invention provides a power source, a means for storing a predetermined first digital signal representative of a desired output signal, a means for providing a second digital signal representative of an operating characteristic of said unit, and a means communicating with said power source and said means for storing and responsive to said first and second signals for producing said desired output signal.

Numerous other aspects, features, objects and advantages of the invention will now become apparent from the following detailed description when read in conjunction with the accompanying drawings, in which:

BRIEF DESCRIPTION OF THE DRAWINGS

FIG. 2 shows an electrical circuit diagram of the basic hybrid cascode amplifier according to the invention;

FIG. 3 is a detailed electrical schematic of the hybrid cascode power amplifier of the preferred embodiment of the invention shown in FIG. 1C;

FIG. 8 is a partial sectional view of the monopolar transformer utilized in the embodiment of FIG. 4;

FIG. 9 is an external view of the transformer of FIG. 8;

FIG. 10 is a partial sectional end view of the transformer of FIG. 9;

FIG. 11 is a detailed electrical schematic of a portion of the Power Supply of the embodiment of the invention in FIG. 1A;

FIG. 12 is the power-on reset circuitry of the embodiment of the invention shown in FIG. 1A;

FIG. 13 is a detailed electrical schematic of the lamp/relay register of the embodiment of the circuitry shown in FIG. 1A;

FIG. 15 and FIG. 16 show a detailed electrical schematic of the Base Voltage Generator/Driver of the embodiment of the invention shown in FIG. 1B.

FIG. 17 is a detailed electrical schematic showing the connections to the microprocessor in the embodiment of the invention shown in FIG. 1A;

FIG. 18 is a block diagram of the microprocessor; and

DESCRIPTION OF THE PREFERRED EMBODIMENT

Figure 1A:
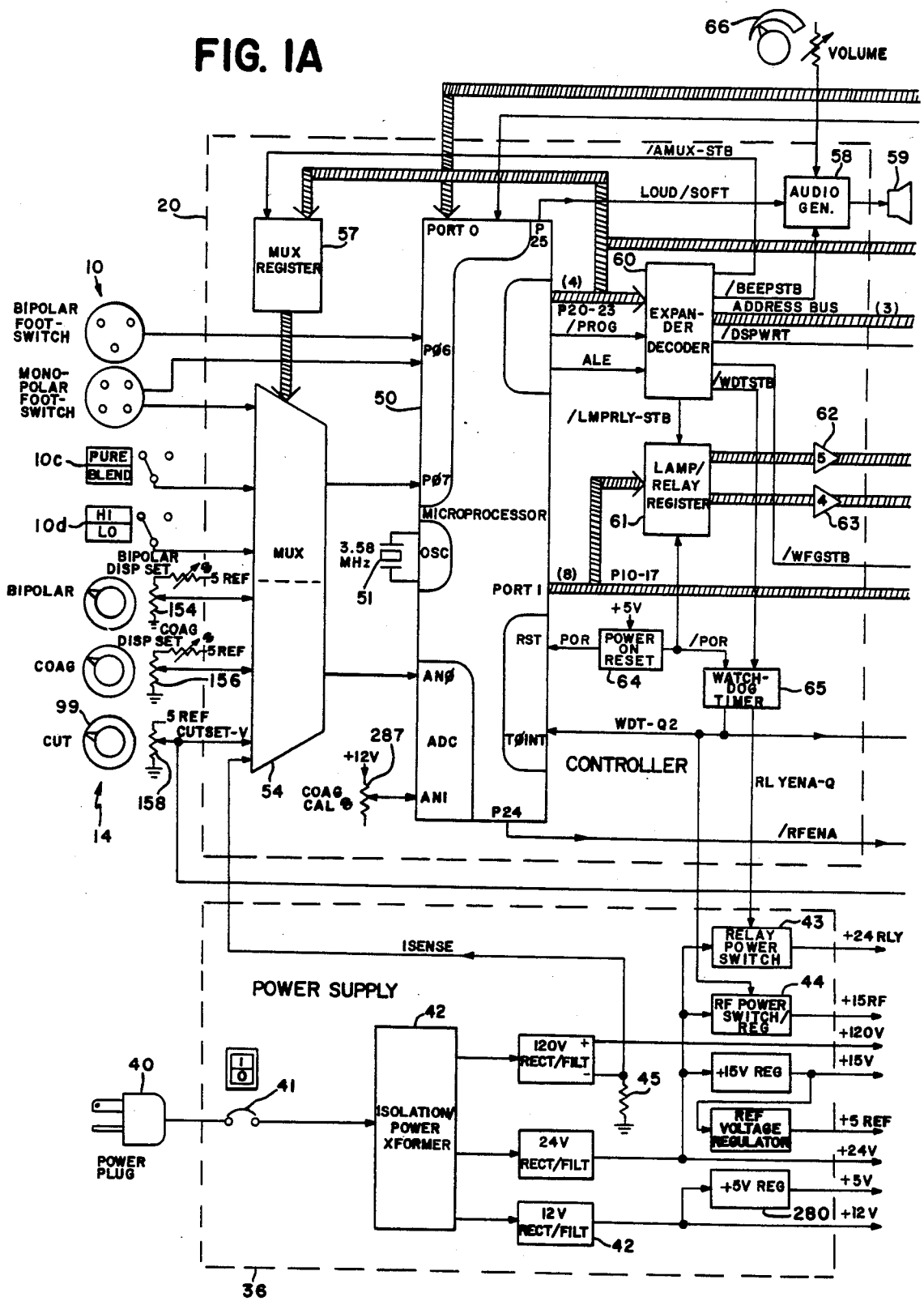
FIGS. 1A through 1C are a block diagrammatic illustration of a preferred embodiment of the invention; the full electrosurgical unit may be seen by placing FIG. 1A on the left, FIG. 1B in the center and FIG. 1C on the right, in which positions the interconnections between the Figs. are evident.
Figure 1B:
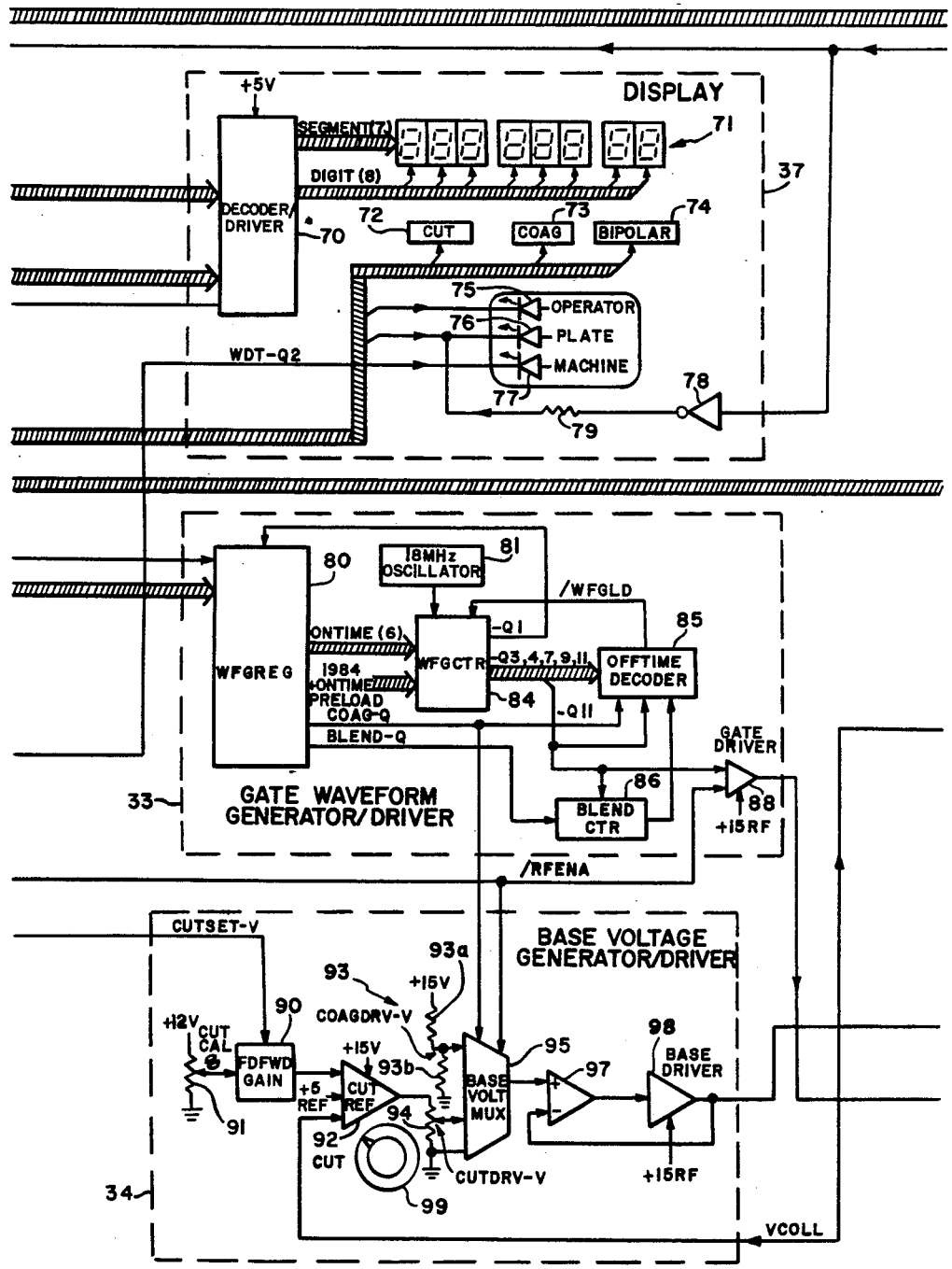
Figure 1C:
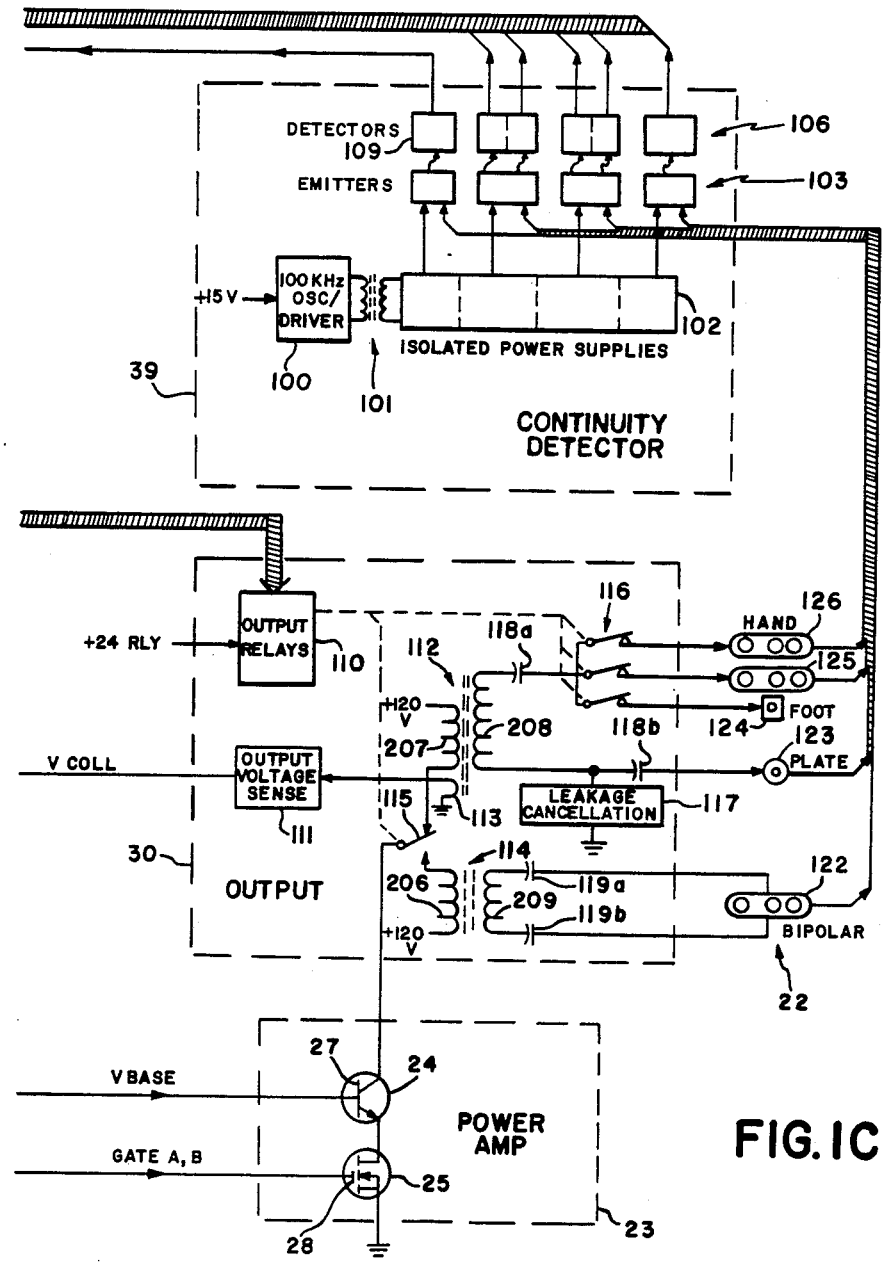

Referring to FIGS. 1A through 1C, an electrosurgical unit according to the preferred embodiment of the invention is shown. The blocks shown are divided along functional boundaries. The schematic diagrams in the following Figs. are divided along the same functional lines where possible. Connections across physical boundaries are shown where they apply. Foot switches 10, hand switches (not shown) connected through outputs 22, front panel switches 10c and 10d and potentiometers 14 (FIG. 1A) control controller circuitry 20 to provide desired electrical mode settings within the unit and thus control the electrical power signals at outputs 22 (FIG. 1C). Cut and Coagulation mode settings are activated via the handswitches and the footswitches 10 which are conventional in electrosurgical units and will not be described further herein. A power amplifier 23 provides the electrical power to the outputs 22 through output circuitry 30. Controller 20 and Gate Waveform Generator/Driver 33 comprise one preferred embodiment of a feedforward means responsive to voltage fluctuations (input at the AN1 port of microprocessor 50) at the power source 36 for producing a regulation signal. Another preferred embodiment of such a feedforward means comprises Base Voltage Generator/Driver 34. In the later embodiment the power source voltage enters the feedforward means at the +12 V input to potentiometer 91 (FIG. 1B). In both embodiments the power supply voltage fluctuations are used to control a regulation signal (VGATE in the former embodiment and VBase in the latter) which is applied to a transistor control terminal (gate 28 in the former embodiment and base 27 in the latter) in amplifier 23 to regulate the output. Outputs 22 are conventional electrosurgical connectors for the particular electrodes indicated, and comprise a means for electrically connecting the output circuitry 30 and the amplifier means 23 to electrosurgical electrodes.

The power for the electrosurgical unit is provided by Power Supply (source) 36 (FIG. 1A). The Power Supply 36 converts the AC mains power to the various DC supply voltages required by the circuitry.

In one aspect of the invention, switches 10 and 10c, potentiometers 14 and multiplexer 54 comprise a means for producing a predetermined first digital signal representative of a desired characteristic of the unit. In this aspect of the invention a portion of power supply 36 (shown in FIG. 11) comprises a means for producing a second digital signal representative of an operating characteristic of the electrosurgical unit.

The Controller 20 embodies the intelligence of the unit. It responds to user commands, communicates with the user via displays and tones, directs and supervises the activities of all other modules in the system, performs fault detection and aids in diagnosis. The Controller 20 includes a memory 50a (FIG. 18) which is a means for storing the signal representative of a desired characteristic of the unit.

The Display 37 provides the user with visual indications of current power settings for each mode, Pure/Blend mode selection, Bipolar Hi/Lo mode selection, which mode is currently activated and indication of fault conditions requiring the user's attention.

The Gate Waveform Generator/Driver 33 (WFG) produces the FET gate 28 drive signals, with a duty cycle determined by line voltage, for the power amplifier under control of the microprocessor 50.

The Base Voltage Generator/Driver (BVG) 34 supplies base current to the power amplifier bipolar transistors 24 at a voltage appropriate to the mode of operation.

In one aspect of the invention, the WFG 33 and the portions of the Controller 20 other than memory 51a comprise a means responsive to a first digital signal and a second digital signal for controlling an output means of the electrosurgical unit. In another aspect of the invention the BVG 34 and the portions of the Controller 20 other than the memory 50a comprise such a means for controlling an output means.

The Power Amp (PA) 25 responds to its input signals in a fashion necessary to produce therapeutically useful RF currents.

The RF Output circuitry 30 transfers the RF power generated by the power amplifier 23 to the output connector panel.

In one aspect of the invention the display 37 comprises an information output means of the unit. In another aspect of the invention the Power Amp 25 and the output circuitry 30 comprise a therapeutic output means of the electrosurgical unit.

The Continuity Detector 39 delivers to the microprocessor 50 the status of various contacts (not shown) in the isolated RF output circuit. The contacts are those of the conventional hand-switchable bipolar and active monpolar accessories and the two wire patient plate circuit, which are connected to outputs 22.

We turn now to a more detailed description of the electrosurgical unit, while referring to FIGS. 1A through 1C. The names such as /PROG and ALE on the lines connecting blocks indicate the designation of the signal which shall be useful in the discussion of the operation of the unit below. The / in front of a signal such as in /PROG indicates the inverted signal. Power Supply 36 is connected to an AC outlet by power plug 40. The unit is turned on or off via switch 41 between power plug 40 and isolation power transformer 42. Power Supply 36 converts the AC outlet power to the various DC supply voltages required by the unit. The nominal supply values are shown at the right of power supply 36 in FIG. 1A, and include two switched power supplies 43 and 44 which enhance the safety of the unit.

Controller 20 includes microprocessor 50, the timing for which is provided by a crystal oscillator 51. A signal from the 12 volt unregulated output of power supply 36 is applied to the microprocessor 50 at input AN1. Controller 20 further includes multiplexer 54 which multiplexes and feeds the signals from controls 10 and 14 to microprocessor 50. Controller 20 also includes multiplexer register 57, audio generator 58, expander-decoder 60, lamp/relay register 61 and associated buffers 62 and 63, power on reset circuitry 64 and watchdog timer 65. A signal, ISENES, is supplied to multiplexer 54 from power supply 36 which is representative of the current drawn from the 120 volt power supply output. This is calibrated by current sense resistor 45. Control signals for the multiplexer 54 are provided from the microprocessor 50 and expander-decoder 60 outputs via multiplexer register 57. Audio generator 58 is controlled via outputs from microprocessor 50 and expander-decoder 60 to produce a signal to drive speaker 59. The volume of the audio generator 58 is controlled via volume control 66 and a loud/soft signal generated by microprocessor 50. Expander-decoder 60 receives output signals from microprocessor 50 which are demultiplexed by expander-decoder 60 using synchronization signals /PROG and ALE which are also provided to expander-decoder 60 by microprocessor 50. The output signals of expander-decoder 60 are provided to multiplexer register 57, audio generator 58, the decoder/driver 70 of the display circuitry 37 (FIG. 1B) the Gate Waveform Generator register 80, the watchdog timer 65 and the lamp/relay register 61. The lamp/relay register 61 receives output signals from microprocessor 50, expander-decoder 60, and power-on reset circuit 64 and in turn applies output signals to display circuitry 37 (FIG. 1B) and output circuitry 30 (FIG. 1C) via buffers 62 and 63 respectively. The power-on reset circuitry applies signals to the lamp relay register 61, the microprocessor 50, and the watchdog timer 65. The watchdog timer 65 uses its own internal timing signals and the inputs from expander-decoder 60 and power-on reset 64 to provide control signals to power relay switches 43 and 44 and microprocessor 50. The microprocessor 50 also receives input signals from continuity detector 39 (FIG. 1C) and applies control signals to gate driver 88 and base voltage multiplexer 95 (FIG. 1B).

Turning now to the circuit of FIG. 1B, the Display circuitry 37 includes decoder/driver 70, seven segment LED display 71, mode indicators 72, 73 and 74, alarm indicators 75, 76, and 77, inverter 78, and resistor 79. The signals from the microprocessor 50 and expander-decoder 60 are decoded by the decoder/driver 70 which in turn drives display 71. Signals from the lamp-/relay register 61 drive mode indicator 72, 73, and 74 and alarm indicator 75 and 76. A signal from the detector 109 is also applied to the plate alarm indicator 76 via inverter 78 and resistor 79. A signal from the watchdog timer 65 drives machine alarm indicator 77.

The Gate Waveform Generator/Driver circuitry includes waveform generator register 80, 18 MHz oscillator 81, waveform generator counter 84, offtime decoder 85, blend counter 86, and gate driver 88. The waveform generator register 80 receives inputs from microprocessor 50, expander-decoder 60, and waveform generator counter 84 and applies control signals to waveform generator counter 84, OFFTIME decoder 85, base voltage multiplexer 95 and blend counter 86. The waveform generator counter 84 receives a timing signal from oscillator 81, the preloaded ONTIME signal from waveform generator register 80, and a signal from OFFTIME decoder 85 and in turn provides signals to waveform generator register 80, OFFTIME decoder 85, blend counter 86 and gate driver 88. The blend counter receives the above-indicated signals and applies a signal to the OFFTIME decoder 85 which in turn applies a signal to waveform generator counter 84 in response to the signals previously described. The signals from the waveform generator counter 84 and the microprocessor 50 control the gate driver 88 to produce the gate drive output signal which is applied to the gate of the field effect transistors 25 in the Power Amplifier 23.

Base Voltage Generator/Driver 34 comprises feed forward gain compensator 90, cut power calibration potentiometer 91, cut reference voltage amplifier 92, coag drive voltage divider 93 comprising resistors 93a and 93b, cut drive voltage potentiometer 94, base voltage multiplexer 95, operational amplifier 97, and base driver amp 98. A voltage signal produced by potentiometer 91 is applied to feed forward gain compensator 90 which in turn applies a voltage to cut reference amplifier 92. Other inputs to cut reference amplifier 92 are the +5 reference voltage and a voltage signal, VCOLL from the output voltage sense circuitry 111 in output stage 30 (FIG. 1C). Resistor 93a is connected between voltage divider 93 and the +15 power supply while resistor 93b is connected between the ground and the voltage divider. The output of cut reference operational amplifier 92 is applied to the base voltage multiplexer 95 through potentiometer 94 which is controlled by cut power control 99. The other side of potentiometer 94 and the base voltage multiplexer 95 are connected to ground. The control signals for the base voltage multiplexer 95 are provided by outputs of gate waveform generator register 80 and microprocessor 50. The output of base voltage multiplexer 95 is applied to the non-inverting input of operational amplifier 97, while the inverting input is connected via a voltage divider (FIG. 15) to the output of base driver 98. The output of operational amplifier 97 is applied to the input of base driver 98 and the +15 volt RF power supply is also applied to base driver 98. The output of base driver 98 is applied to the base of the bipolar transistors 24 in power amp 23.

Turning now to FIG. 1C, Continuity Detector 39 comprises 100 KHz oscillator/driver 100, toroidal transformer 101, isolated power supplies 102, emitters 103, and detectors 106. The oscillator driver 100 drives the primary circuit of transformer 101, the secondaries of which in turn drive isolated power supplies 102. The outputs of the power supplies 102 are applied to the emitters 103 which are also connected to the switches (not shown) for the hand, foot, plate, and bipolar electrodes through connectors 22. The light from the emitters 103 is detected by detectors 106. Detector 109 which is associated with the emitter which is connected to the plate electrode is applied to the plate alarm indicator 76 as indicated above, and also to the microprocessor 50. The outputs of detectors 106 are applied to microprocessor 50.

Output stage 30 comprises output relays 110 (which include switches 115 and 116), output voltage sense circuitry 111, monopolar transformer 112 which includes a sense winding 113, bipolar transformer 114, and four capacitors such as 118a. The inputs to the output relays are from the lamp/relay register 61 (FIG. 1A) and the 24 volt relay output voltage. The physical connection between the output relays and the switches 115 and 116 is shown by a dotted line. One side of both monopolar and bipolar transformers 112 and 114 is connected to the +120 volt unregulated power supply while the other side is connected to Power Amp 23 through switch 115. One side of sense winding 113 is connected to ground while the other side is applied to output voltage sense circuitry 111. One side of secondary 208 of monopolar transformer 112 is connected to the outputs 124, 125, and 126 for the hand and foot controlled monopolar electrodes through switches 116 and capacitor 118a. The other side is connected to ground through the leakage cancellation circuitry 117 and to the plate electrode output 123 through capacitor 118b. One side of the secondary 209 of bipolar transformer 114 is connected to one of the terminals of bipolar output 122 through capacitor 119a while the other side is connected to another of the terminals of bipolar output 122 through capacitor 119b.

The Power Amplifier circuitry 23 has already been discussed above and will be discussed in considerably more detail below.

FIG. 2 shows a simplified embodiment of the basic hybrid cascode amplifier of the present invention. The simplified circuitry of FIG. 2 will be useful in understanding the preferred embodiment of the hybrid cascode amplifier which is shown in FIG. 3. In the basic amplifier of FIG. 2 the FET device 25 and the bipolar device 24, a diode 130 and the electrosurgical unit load 131 (which is the amplifier load) are connected in series between ground and the +120 volts power supply. More particularly, the source terminal 25a of the FET 25 is connected to ground while the drain 25b of the FET 25 is connected to the emitter 24a of the bipolar transistor 24. The collector 24b of the bipolar transistor 24 is connected to the cathode of the diode 130 while the anode of the diode is connected to one side of the load 131. The other side of the load is connected to the positive voltage supply. The control terminal or gate 28 of FET 25 is connected to a voltage source 134 designated VGATE which in terms of the preferred embodiment of the present invention is the output signal of the Gate Waveform Generator/Driver circuitry 33 (FIG. 1B). The other side of the voltage source 134 is connected to ground. The control terminal or base 27 of bipolar transistor 24 is connected to a voltage source designated as VBASE through resistor 137 which is designated Rb. In terms of the preferred embodiment of the invention, the voltage source 139 is the output signal of the Base Voltage Generator/Driver 34. The other side of the voltage source 139 is connected to ground. The base 27 of bipolar device 24 is also connected to ground through capacitor 135 designated as Cb. This is a bypass capacitor which stores the turnoff charge of bipolar device 24.

Turning now to FIG. 3, the hybrid cascode stage of the preferred embodiment of the invention is shown. It consists of two separate hybrid cascode sections connected at the collector bus 144. One section comprises FET 146 and bipolar transistors 147, 148, and 149, while the other section comprises FET 152 and bipolar transistors 153, 154, and 155. Since the circuitry associated with each of the FETs is identical, and the circuitry associated with each of the bipolar transistors is identical, the circuitry shall be described for only the FET 146 and the transistor 148. The circuitry associated with FET 146 comprises zener diode 157 and resistors 158 and 159. The cathode of diode 157 is connected to the line 160 carrying the incoming gate drive voltage, while its anode is connected to the source, S, of FET 146. Resistor 158 is connected between the cathode of diode 157 and the gate of FET 146 in the line 160 carrying the gate voltage to the gate. Resistor 159 is connected between the gate, G, of FET 146 and the anode of diode 157. The anode of diode 157 and the source, S, of FET 146 are grounded. The circuitry associated with transistor 148 includes resistor 162, capacitors 163 and 164, fuses 165 and 168, resistor 166, and diode 167. Resistor 162 is connected between the drain, D, of FET 146 and the emitter, E, of transistor 148. Fuse 165 is connected along the line 169 carrying the base drive voltage VBASE to the base, B, of transistor 148. Resistor 166 is also connected along the base voltage input line 169 between fuse 165 and base, B. Capacitor 163 is connected between line 169 and ground at a point between fuse 165 and resistor 166, while capacitor 164 is connected between base, B, and ground. The cathode of diode 167 is connected to the collector, C, of transistor 148 while the anode of the diode is connected to one side of fuse 168. The other side of fuse 168 is connected to the collector bus 144. The drain, D, of FET 146 is connected to the anode of diode 171 and the cathode of the diode is connected to the 120 volt voltage source through resistor 172. Zener diode 173 and capacitor 174 are connected in parallel between the cathode of diode 171 and ground, with the anode of diode 173 being connected to the ground side. Likewise, the line 169 is connected to ground through a parallel zener diode 176 and capacitor 177, with the anode of diode 176 being toward the ground side. The collector bus 144 is connected to the output circuit (FIG. 4).

Figure 4:
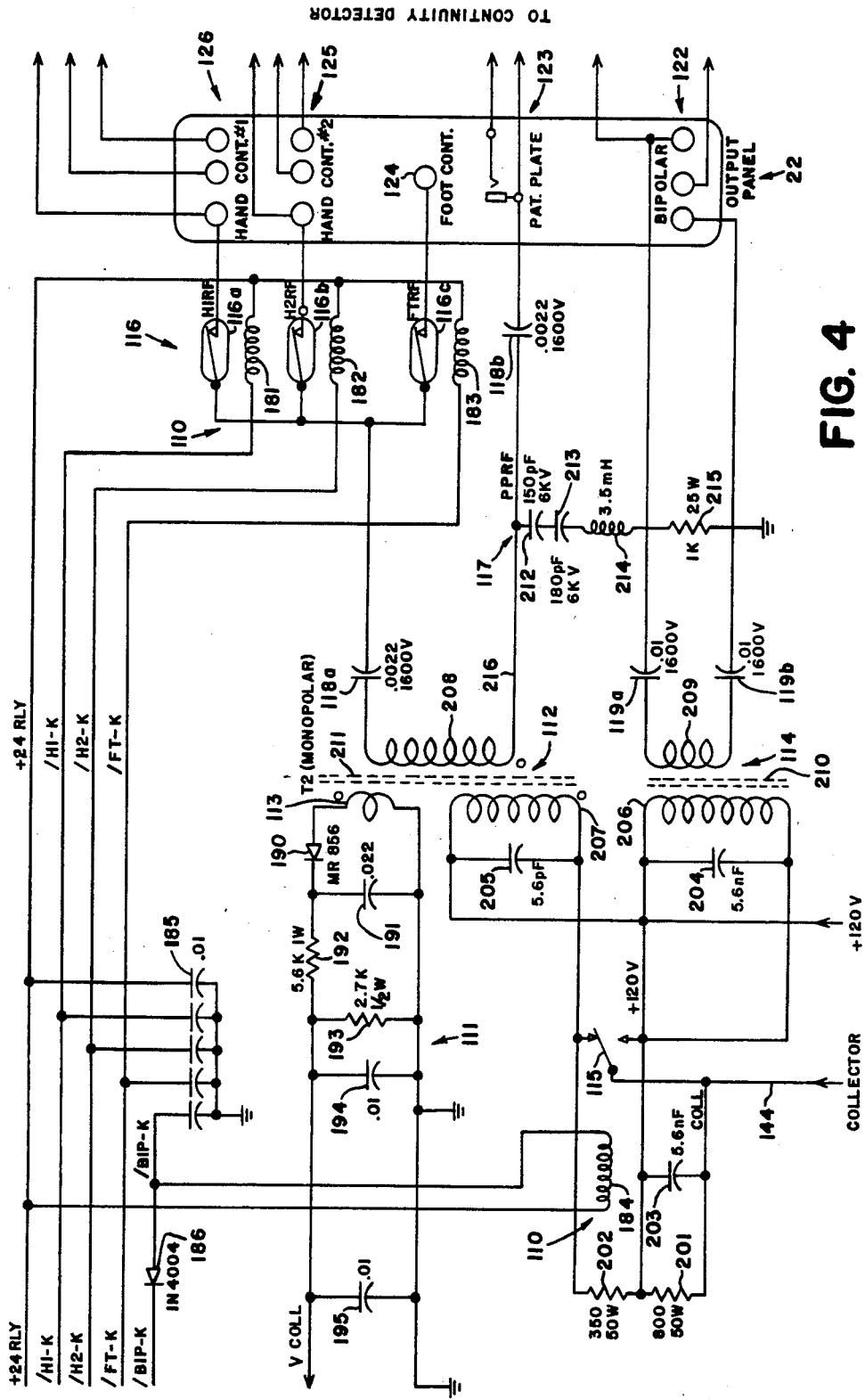
FIG. 4 is a detailed circuit electrical schematic of the output stage of the embodiment of the invention shown in FIG. 1C.

Turning to FIG. 4, the collector bus is connected to either the monopolar transformer 112 or the bipolar transformer 114 depending upon the position of switch 115. Much of the output circuit 30 of FIG. 4 has been discussed in reference to FIG. 1c, and thus we shall here discuss only those aspects of the circuit which were not discussed therein. The output relay circuitry 110 includes relay coils 181, 182, and 183 which act on the corresponding relay contacts 116A through 116C and coil 184 which acts on contact 115. The relay coils 181 through 183 are connected between the input lines /H1−K, /H2−K, /FT−K respectively, and the +24 relay supply voltage. Coil 184 is connected between the /BIP−K input line and the +24 relay supply voltage. Diode 186 is connected in series with the coil 184 along the /BIP−K input line with its anode toward the coil. Capacitors, such as 185, are connected between each of the four input lines and ground. The input lines are connected to the corresponding signal lines shown as outputs (TO OUTPUT) in FIG. 13.

The output voltage sense circuitry 111 includes SENSE winding 113, diode 190, capacitors 191, 194, and 195, and resistors 192 and 193. The anode of diode 190 is connected to one side of the SENSE winding 113, while the cathode is connected to the anode of diode 415 (FIG. 16) through resistor 192. The other side of SENSE winding 113 is connected to ground. Capacitor 191 is connected between the cathode of diode 190 and the ground line from the SENSE winding 113. Resistance 193 and capacitors 194 and 195 are connected in parallel between the VCOLL voltage line and the ground line.

The transformer primary circuitry includes resistors 201 and 202 and capacitors 203, 204, and 205. Resistor 201 and capacitor 203 are connected in parallel between the 120 volt supply voltage line and the collector bus line. Resistor 202 is connected between the 120 volt line voltage line and the side of primary 207 to which the collector bus is applied. Bipolar transformer 114 includes primary 206, secondary 209, and core 210. Monopolar transformer 112 includes primary 207, secondary 208, and core 211.

The leakage cancellation circuitry 117 includes capacitors 212 and 213, inductance 214, and resistance 215. The four are connected in series, in the order just given, between the side of the monopolar secondary which goes to the patient plate and ground.

Figure 5:
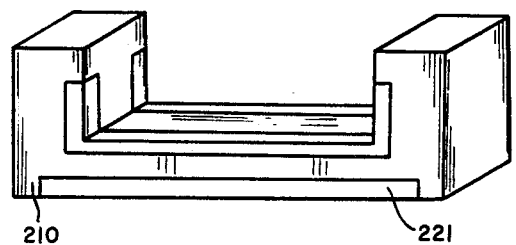
FIG. 5 shows the core of the bipolar transformer utilized in the embodiment of FIG. 4.
Figure 6:
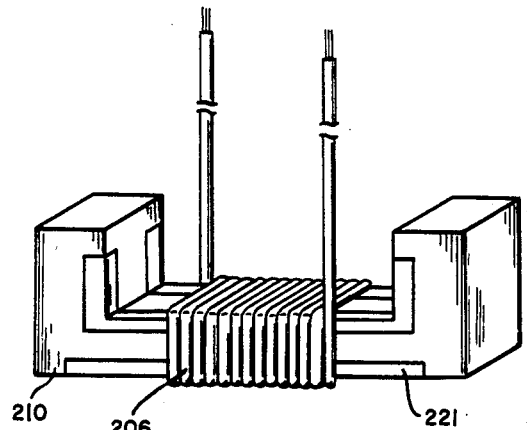
FIG. 6 illustrates the method of winding the primary winding on the core of FIG. 5.
Figure 7:
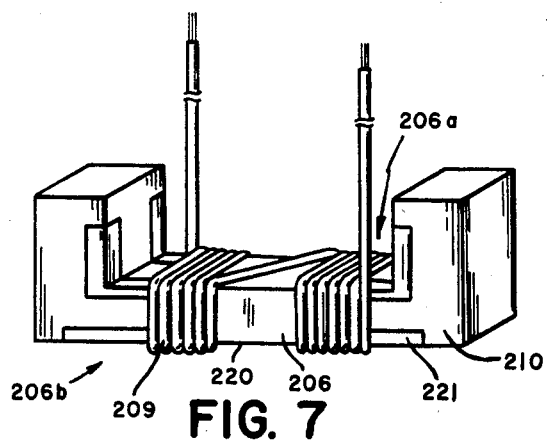
FIG. 7 shows the method of winding of the secondary winding on the core of FIG. 5.

Turning now to FIGS. 5 through 10, the construction of the transformers shall be disclosed in detail. The construction of the bipolar transformer 114 is shown in FIGS. 5 through 7. The unwrapped core 210 is shown in FIG. 5. The portion of core 210 which will contact primary 206 and secondary 210, is covered with insulating tape 221. FIG. 6 shows the winding of the preferred 12 turns of the primary 206 on the core 210. FIG. 7 shows the winding of the preferred 13 turns of the secondary 209 on the core 210. Preferably, the primary and secondary are wound concentrically about the same axis, six turns of the secondary 209 are wound at one end 206a of the primary 206, another six turns are wound at the other end 206b, and there is one turn crossing over the primary 206. The primary is covered by a layer of insulating tape 220 in FIG. 7. After the secondary is wound, it is also covered by insulating tap.

FIGS. 8, 9, and 10 show the construction of the monopolar transformer. The transformer is built on a nonconductive bobbin 229 which consists of a hollow cylinder 230 having four dividers 231, 232, 233, and 234 attached to its outer surface. The shape of the dividers is rectangular on one end and circular on the other as shown best in FIG. 10. The primary winding 207 is wound between the center dividers 232 and 233 with the ends of the primary 207 passing through holes such as 251 (FIG. 9) in the dividers. The secondary winding 208 is wound between the dividers 231 and 232 and then passes through holes 253 and 254 in dividers 232 and 233 respectively, crossing the primary winding 207, and is then wound between dividers 233 and 234. Thus as in the bipolar transformer, the primary 207 and secondary 208 are wound concentrically and a first portion 208a of the secondary 208 is wound at one end 207a of the primary 207, while a second portion 208b of the secondary 208 is wound at the other end 207b of the primary 207. The ends of the secondary are looped through holes, such as 256, in the dividers 231 and 234. Each of the windings are covered with insulated tape, 235. Preferably the primary winding has 7½ turns of wire with the direction of the winding passing from front to rear at the lower portion of FIG. 8. Preferably the second winding has 27 turns with 8 turns in the first layer 258, 7 turns in each of the second and third layers and 5 turns in the fourth and outer layer. It is preferably wound in a counter-clockwise direction passing from right to left in FIGS. 8 and 9. The core 211 of the monopolar transformer consists of four cylindrical ferrite core pieces 240, 241, 242, and 243 which fit inside of cylinder 230 of bobbin 229. The core pieces 240 through 243 have a cylindrical bore passing through their centers. Rod 246 having threaded ends passes through the centers of core pieces 240 through 243. Nonconductive washers 244 and 245 fit over the ends of bobbin cylinder 231 and are held in place by nuts 247 and 248 which are screwed on to the ends of rod 246. Hot melt adhesive 233 is melted into one end of cylinder 231 to hold the cores 211 firmly in position. SENSE winding 113 is preferably a single wind about primary 207, preferably at the end of the primary 207 connected to the 120 volt line rather than the end connected to the collector, again wound in the counter-clockwise direction. The ends of SENSE winding 113 are twisted together as shown at 259.

Turning now to FIGS. 11 through 15, detailed circuitry pertaining to the inventive aspects of the electrosurgical unit are shown. FIG. 11 shows the details of the 12 volt unregulated power supply and the production of a signal, AN1, which is fed into the microprocessor, and used by the microprocessor to regulate the duty cycle of the coagulation and bipolar outputs to produce a uniform output power despite variations of the mains voltage. The circuitry of FIG. 11 comprises a means for producing a second signal representative of an operating characteristic of the electrosurgical unit. This signal is digitized by the A/D converter 50h (FIG. 18) in the microprocessor as will be discussed below. The power supply circuitry includes AC plug 40, a lighted circuit breaker 41 which includes single pole double throw breaker switch 41a and 41b, resistor 268 and light 267 which indicates the on or off condition of the circuit breaker 41, transformer 42a, bridge rectifier 272, and capacitors 275 through 277. The symbol 273 indicates that the two wires are a twisted pair. Voltage regulator 280 and capacitor 281 comprise circuitry to produce the 5-volt regulated power supply. The green wire of plug 40 is connected to chassis, the white wire is connected to one side of primaries 270a and 270b through circuit breaker 41a, while the black wire is connected to the other side of the primaries through circuit breaker 41b and thermofuse 269. The two outputs of the transformer secondary 270c are applied across bridge rectifier 272.

Capacitors 275, 276, 277, and 281 are connected in parallel across the outputs of bridge rectifier 272. The negative output of rectifier 272 is grounded and the positive output provides the 12-volt unregulated power supply. The positive output of bridge 272 is also applied to the input of voltage regulator 280, while the common line is attached to the negative side of the rectifier 272 which is grounded. The output of voltage regulator 280 provides the 5-volt regulated power supply. The circuitry for providing a signal representative of the unregulated 12-volt power supply, which varies directly as the mains voltage, as a control signal to the microprocessor comprises resistors 284, 286, 290, and 291, capacitors 285, and 292, and potentiometer 287. The 12-volt power supply is applied to one side of resistor 284 and the other side is grounded through capacitor 285 and also connected to resistor 286. The other side of resistor 286 is connected to one input and the output of potentiometer 287. The other input of potentiometer 287 is grounded through resistor 290. The output of potentiometer 287 is applied through resistor 291 to the microprocessor (FIG. 1A) to provide the input signal for power regulation. The output line 293 is grounded through capacitor 292.

FIG. 12 shows the details of the power-on reset circuitry which insures orderly power up of the electrosurgical unit. It includes capacitor 297, resistor 298, diode 299, three input NAND GATE 300, and inverter 304. The three inverted inputs of NAND GATE 300 are connected to ground through capacitor 297 and the 5-volt power supply through resistor 298. They are also connected to the 5-volt power supply through diode 299, with the cathode of the diode toward the power supply. The output of NAND GATE 300 provides the POR signal to microprocessor 50 and is also applied to the input of inverter 304. The output of inverter 304 provides the /POR signal to the lamp/relay register 61 and the watchdog timer 65.

FIG. 13 shows detailed circuitry of the lamp/relay register 61 and the gate waveform generator register 80, both of which receive the P10 through P17 signals from the microprocessor 50. In FIGS. 13 through 17 the numeric characters located adjacent to the inputs and outputs of an integrated circuit chip such as 61a (in the center of FIG. 13), for example the number 11 at the upper left hand corner of chip 61a, indicate the pin number of the input or output of that particular chip. The alphabetic or alphanumeric characters on the incoming lines, such as LMPRLYSTB on the line coming into input 11 of chip 61a or P10 coming into input 17 of the same chip, are the names of the signals that are applied to the lines. The alphanumeric characters on the inside of the chip and adjacent to the inputs and outputs, such as the D0 which is opposite the number 17 input of chip 61a, indicate the names of the signals for processing purposes within the chips. The numbers of the input and output terminals are useful for determinig the connections between the chips, while the signal names will be useful in describing the operation of the chips below.

The lamp relay register 61 includes octal buffer 61a and 8 inverters, 7 of which (61b through 61c) are part of an O-C buffer. The terminal numbers of the inverters correspond to the inputs and outputs of the buffer. The /LMBRLYSTB signal from the expander-decoder is applied to the number 11 input of buffer 61a and the P10 through P17 signals from the microprocessor 50, emanating from the 25 through 32 output terminals of the microprocessor, are applied to the 17, 18, 14, 13, 4, 7, 8, and 3 inputs respectively of buffer 61a. The /POR signal is applied to the inverted 1 input of buffer 61a. The 16, 19, 15, 12, 5, 6, 9, and 2 outputs of buffer 61a are connected to the 2, 1, 3, 4, 7, 6, 5, and 9 inputs respectively of buffer 61b. The 15, 16, 14, and 13 outputs of buffer 61b provide the /BIP−K, /H1−K, /H2−K, and /FT−K signals respectively. The connections of these outputs of buffer 61b can best be seen by following the signals indicated to the output circuitry of FIG. 4 and noting the connections, which were discussed above. The 15, 10, and 11 outputs of buffer 61b are connected to the bipolar, coag, and cut lights respectively in the display. The 12 output of buffer 61b is applied to the patient plate light in the display, while the output of inverter 61d is applied to the operator light in the display. The register 80 is included in FIG. 13 in order to more easily note the terminals to which the P10 through P17 signals from the microprocessor 50 are applied, but will be discussed in FIG. 14 where they are shown in more detail.

Figure 14:
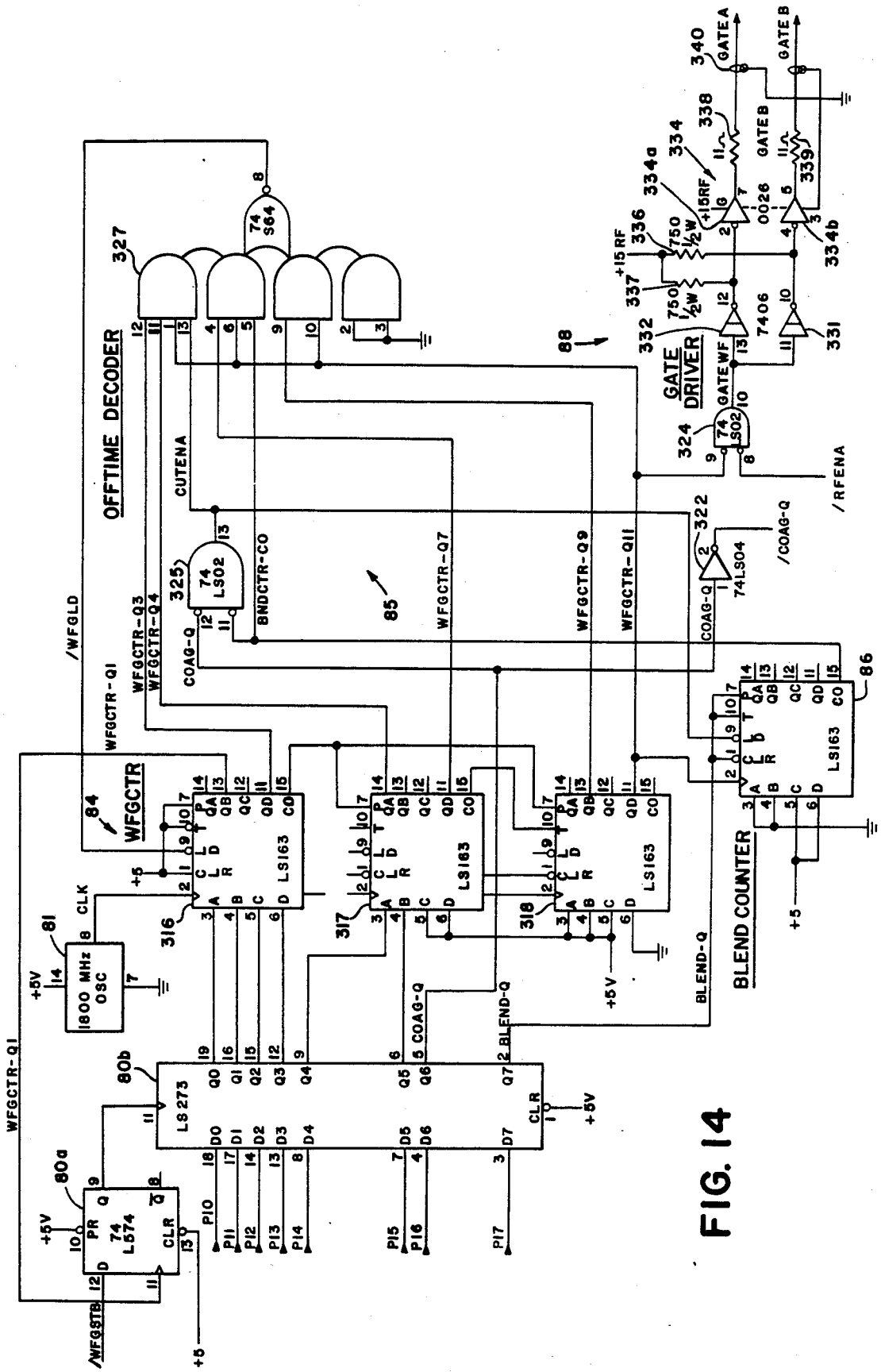
FIG. 14 is a detailed electrical schematic of the Gate Waveform Generator/Driver of the embodiment of the invention shown in FIG. 1B.

Turning now to FIG. 14, the Gate Waveform Generator/Driver circuitry is shown in detail. The circuitry includes dual D flip flop 80a, octal buffer 80b, crystal oscillator 81, 4 bit counters 316, 317, 318, and 86, inverter 322, NOR gates 324 and 325, AND/OR inverter 327, inverters 331 and 332, clock drivers 334a and 334b, and resistors 338 and 339. The symbol at 340 indicates that the two wires associated with the loop are coaxial cable. The 10 and 13 inputs of flip flop 80a are connected to the 5-volt power supply. The /WFTSTB signal from the expander-decoder 60 is applied to the 12 input of flip flop 80a. The number 13 output of 4 bit counter 316 is connected to the 11 input of flip flop 80a. The number 9 output of flip flop 80a is connected to the 11 input of buffer 80b. The 18, 17, 14, 13, 8, 7, 4, and 3 inputs of buffer 80b are connected respectively to the 25 through 32 outputs of microprocessor 50. The inverted 1 input of buffer 806 is connected to the 5-volt power supply. The 19, 16, 15, and 12 outputs of buffer 80b are connected to the 3, 4, 5, and 6, inputs respectively of counter 316. The 9 and 6 outputs of buffer 80b are connected to the 3 and 4 inputs respectively of counter 317. The 5 and 6 inputs of counter 317 and the 3, 4, 5, inputs of counter 318 are connected to the 5-volt power supply, while the 6 input of counter 318 is grounded. The 2 output of buffer 80b is connected to the 1, 10 and 7 inputs of counter 86. The 3 and 4 input of counter 86 are grounded while the 5 and 6 inputs are connected to the 5-volt power supply. The 14 input of oscillator 81 is connected to the 5-volt power supply, while the 7 input is grounded. The 8 output is connected to the 2 inputs of counters 316, 317, and 318. The 1 and 10 inputs of counters 316, 317, and 318, and the 7 input of counter 316 are all connected to the 5-volt power supply. The 7 inputs of counters 317 and 318 are connected to the 15 output of counter 316. The 9 inputs of counters 316, 317, and 318 are connected to the 8 output of AND-OR-invert gate 327. The 11 output of counter 316 is connected to the 12 input of AND-OR-invert gate 327. The 14 and 11 outputs of counter 317 are connected to the 11 and 4 inputs respectively of AND-OR-invert gate 327. The 15 output of counter 317 is connected to the 10 input of counter 318. The 13 output of counter 318 is connected to the 9 input of AND-OR-invert gate 327. The 11 output of counter 318 is connected to the 2 input of counter 86, the 9 input of NOR gate 324, and the 1, 6, and 10 inputs of AND-OR-invert gate 327. The 6 output of buffer 80b is connected to the 12 input of NOR gate 325 and the input of inverter 322. The output of counter 86 is connected to the 11 input of NOR gate 325 and 5 input of AND-OR-invert gate 327. The 13 output of NOR gate 325 is connected to the 9 input of counter 86 and the 13 input of AND-OR-invert gate 327. The 2 and 3 inputs of AND-OR-invert gate 327 are grounded. The output of inverter 322 provides the /COAG−Q signal which will be discussed in reference to FIG. 15. The /RFENA signal from the 38 output of microprocessor 50 is applied to the 8 input of NOR gate 324. The 10 output of NOR gate 324 is applied to the inputs of inverters 331 and 332. The outputs of inverters 331 and 332 are applied to the inputs of drivers 334a and 334b respectively. The inputs of drivers 334a and 334b are also tied to the +15-volt radiofrequency power supply through resistors 336 and 337 respectively. The 3 input of the dual driver 334 is connected to ground and the 6 input is connected to the 15-volt radiofrequency power supply. The dotted line between the drivers 334a and 334b indicate that both are connected to both the ground and 15-volt power supply. The output of driver 334a is applied through resistor 338 to the circuitry of FIG. 3 as the Gate A voltage, while the output of driver 334b is applied through resistor 339 to the circuitry of FIG. 3 to provide the Gate B voltage.

Turning now to FIGS. 15 and 16, the Base Voltage Generator/Driver circuitry is shown. FIG. 15 shows the base voltage multiplexer 95 which includes diodes 352 and 357 (which form an analog OR gate) resistor 358, and FET 360. Open Collector driver 350 and inverter 322 (FIG. 14) also assist in the multiplexing action. The voltage divider circuitry 93 includes resistors 93a, 351 and 93b. The /COAG−Q signal from the output of inverter 322 (FIG. 14) is applied to the input of driver 350. The output of driver 350 is applied to the anode of diode 352 through resistor 351. The line between the output of driver 350 and transistor 351 is connected to the 15-volt regulated power supply through resistor 93a, while the line between resistor 351 and diode 352 is connected to ground through resistor 93b. The cathode of diode 352 is connected to the noninverting input (5 input) of operational amplifier 97. The CUTDRV−V voltage (which is supplied by the circuitry of FIG. 16) is fed into the multiplexer through circuitry including resistors 355, 356. The CUTDRV−V voltage from the output of potentiometer 94 (FIG. 16) is applied to the anode of diode 357 through resistor 356. The line between the output of potentiometer 94 and resistor 356 is grounded through resistor 355. The cathode of diode 357 is connected to the 5 input of driver 97 and also to ground through resistor 358. The /RFENA signal from the 38 output of microprocessor 50 is applied to the gate of FET 360, while the source of the FET is connected to ground and the drain is connected to the line between the cathodes of diodes 357 and 352 and the 5 input of op amp 97. The inverting input (6 input) of the op amp 97 is connected to ground through resistor 365. The 4 input is connected to ground and the 8 input is connected to the 15-volt power supply and to ground through capacitors 363 and 364. The 7 output of op amp 97 is connected to the base of transistor 375 through resistor 372, to the 15-volt power supply through resistor 371, and to the inverting input through capacitor 370. The collector of transistor 375 is connected to the +15-volt RF power supply, and to ground through capacitor 374. The emitter provides the VBASE signal that drives the bases of the transistors of FIG. 3. The emitter of transistor 375 is also connected to the inverting input of op amp 97 through resistor 373 and to ground through capacitor 376. The VBASE line is a coaxial cable the outer conductor of which is grounded.

The CUTDRV−V voltage is provided by the circuitry of FIG. 16. The circuitry includes a dual potentiometer having knob 99 mounted on the front panel which adjusts potentiometers 15 and 94, potentiometer 91, transistor 380, optical isolator 400, operational amplifier 410, capacitors 381, 382, 391, 416, and 417, and resistors 383, 384, 387, 390, 392, 393, 409, 411, and 419 and diode 415. One input of potentiometer 15 is connected to ground while the other is connected to the +5 reference voltage through resistor 387. The output of potentiometer 15 provides the CUTSET—V voltage (FIG. 1A) and is also applied to the base of transistor 380 through resistor 384. Capacitor 381 is connected between the two inputs to potentiometer 15 while capacitor 382 and resistor 383 are connected in parallel between the grounded input and the output. The collector of transistor 380 is connected to the 5-volt power supply while the emitter is connected to ground through the incandescent lamp in optical isolator 400. One input of potentiometer 91 is connected to ground through resistor 393 while the other input is connected to the 12-volt unregulated power supply through resistors 390 and 392. The line between resistors 390 and 392 is connected to ground through capacitor 391. The high input and the output of potentiometer 91 are connected to the inverter input (2 input) of operational amplifier 410 through the photoresistor side of optical isolator 400. The output voltage derived from SENSE winding 113. VCOLL, is applied to the anode of diode 415 which is also connected to ground through capacitors 416 and 417. The cathode of diode 415 is applied to the inverting input of operational amplifier 410. Capacitor 408 and resistor 409 are connected in parallel between the output (1 pin) of operational amplifier 410 and the inverting input. The noninverting input (pin 3) of operational amplifier 410 is connected to the 5-volt reference power supply through resistor 411. The output of operational amplifier 410 is applied to one input of potentiometer 94, while the other input of the potentiometer is grounded through resistor 419. The output of potentiometer 94 provides the CUTDRV−V voltage. The dotted line in FIG. 16 indicates the physical connection of the two potentiometers 15 and 94.

FIG. 17 shows the microprocessor 50, indicating the connections to the microprocessor that have not already been discussed, and also showing the microprocessor signals associated with the various inputs and outputs of the microprocessor. The circuitry directly associated with the microprocessor and not previously discussed in detail includes 3.579 mHz crystal 51, capacitors 426, 429, 433, 434, and 439, and resistors 427, 436, 437, and 438. Crystal 51 is connected between the 22 and 23 inputs of microprocessor 50 in parallel with resistor 427. Microprocessor input 23 in grounded through capacitor 426. Inputs 19, 20 and 7 are grounded. Input 6 which is connected to the multiplexer 54 (FIG. 1A) is also grounded through capacitor 429. Input 21 is connected to ground through capacitor 433 and is also connected to ground through capacitor 434.

Microprocessor output 38 which provides the /RFENA signal is also connected to the 5-volt power supply through resistor 436. Output 37 is inverted to provide the /PROG signal. Inputs 40 and 9 are connected through resistor 438, while input 40 is connected to the 5-volt power supply and resistor 9 is connected to ground through resistor 437. Inputs 3 and 4 are connected to the 5-volt reference power supply and are also connected to ground through capacitor 439.

FIG. 18 shows a block diagram of the microprocessor 50. The microprocessor includes a memory 50a which is a means for storing a first digital signal representative of a predetermined characteristic of the electrosurgical unit. The memory 50a includes a program read-only memory 50b and a data read-write memory 50c. The microprocessor also includes a clock 50d, a central processing unit 50e, a timer/event counter 50f, digital input/output lines 50g, analog/digital converter 50h, and buffers 50a connecting the above parts.

The various electronic parts of the invention are available through most electronic supply houses. The manufacturer's designation of the particular parts used in the preferred embodiment are indicated in the drawings: for example, in FIG. 3, diode 167 is an MR856 diode, transistor 148 is a 430HV transistor, while FET 146 is a IRF131 FET. The values of the resistances, capacitances, fuses and other devices are given next to each one; for example fuse 165 is a ¼ amp fuse, capacitor 163 is a 1.0 microfarad, 63 volt capacitor, and resistor 166 is a 3.3 ohm, 2 watt, resistor. Capacitances are given in microfarads and resistances are given in ohms unless otherwise noted (K after a resistance indicates kiloohms). In FIG. 4, switches 116 are magnetically controlled reed switches. The designations of the various gates, inverters, integrated circuit chips, etc. used in the preferred embodiment, such as the gate 300 and inverter 304 in FIG. 12 and the integrated circuit chip 61a in FIG. 13 are given on the part, such as the designation 4023 of gate 300, or next to the part, such as the designation 74LS04 next to inverter 304. In some instances the designation is put on two lines, such as in the case of quad NOR gate 325 (FIG. 14) in which the designation is 74LS02. The microprocessor 50 is a single chip 8022 microprocessor which is custom-programmed as will be described below. Detailed instructions for programming and using the microprocessor are provided by the manufacturer. The bobbin 229 of monopolar transformer 112 (FIGS. 8–10) is preferably molded of nylon. Cores 210 and 211 are preferably made of TDK H7C4 ferrite. Rod 246 is preferably a #6-32 threaded brass rod and nuts 248 are preferably brass. Washers 244 and 245 are preferably nylon. Primary windings 206 and 207 are preferably #17 Litz wire while secondaries 208 and 209 and sense winding 259 are preferably #24 PVC stranded wire. The tape, such as 220, 221, and 235, is preferably a vinyl tape such as SCOTCH# #33.

We now turn to a description of the operation of the various inventive aspects of the electrosurgical unit. Power supply 36 produces 8 different power outputs, including a 12-volt unregulated supply. The 12-volt unregulated supply is incorporated into feedfoward circuitry for regulating the power the outputs 22. The 12-volt supply is fed into the microprocessor at input 5 to produce the AN1 signal which controls the duty cycle of the power amplifier in the coagulation and bipolar modes to regulate the output power in these modes. The 12-volt unregulated supply is also fed into the optical isolator and the base voltage generator/-driver, as described above, in order to regulate the VBASE voltage to keep the power output constant despite variations in the supply voltage in the cut and blend modes. The operation of these two feedforward circuits shall be described below.

As discussed above, analog signals are applied to the AN0 and AN1 analog input ports of the microprocessor. An analog-to-digital converter (ADC) 50h on board the microprocessor 50 converts the voltage of the external analog signals in the range of 0 to the +5REF voltage to 8-bit internal digital signals in the range 0 to 255. An internal 2:1 analog multiplexer under program control directs one or the other to the ADC. AN0 is further multiplexed under control of the Mux Register 54 among any of the three power control position signals, BIP, COAG or CUTSET−V, and −ISENSE, a 0 to 1.13 volt signal indicating the amount of current drawn from the +120-volt supply. The AN1 input reads a scaled sample of the unregulated +12-volt supply from which the microprocessor 50 infers the AC main voltage in its Coag and Bipolar line-voltage compensation routine. In terms of the discussion above, the digitized AN0 signal is a first digital signal representative of a desired characteristic of the unit, while the digitized AN1 signal is a second digital signal representative of an operating characteristic of the unit.

The microprocessor ADC 50h is ratiometric, that is, it responds to the ratio of an analog input signal to the voltage +5REF appearing on the AVREF pin. As such, signals derived as a ratio of +5REF, such as the set voltages (xxxSET−V) from the power control pots, will be converted accurately regardless of the actual on voltage on +5REF. However, −ISENSE and the signal on AN1 are absolute in nature, so the accuracy of their conversion by the ADC 50h depends upon the accuracy of +5REF. For this reason, +5REF is supplied by 1% regulator 280. The SUBST pin on the microprocessor 50 is tied directly to the IC substrate and helps filter the voltage pulses generated by the internal substrate bias pump. The voltage on SUBST is normally above one volt negative with respect to ground.

The pot position signals, xxxSET−V, are used in all three cases to determine the value displayed on the digital power displays and to calculate the limiting value for −ISENSE. Further, COAGSET−V and BIPSET−V determine the RF power output in those modes via pulse-width commands delivered to the gate waveform generator (see below). The full scale range of BIPSET−V and COAGSET−V is limited to about two-thirds of +5REF to simplify the conversion of these voltages to a waveform generator command. Trimmers 15b and 15c compensate for tolerance variations in the control pots 14 and are set to yield the correct full dial power display. Should a hardware failure in the control pots 14 cause xxxSET−V (CUT, COAG, or BIP) to exceed the normal upper limit at full dial the microprocessor 50 will declare a failure and shut down in lieu of trying to deliver power corresponding to that voltage. Resistor 387 connected to the cut power control pot serves a similar purpose. If a hardware failure elsewhere in the unit cause more power than is set on the pots 14 to be drawn from the power supply 36, this is reflected in −ISENSE and the microprocessor likewise will shut down.

The sensed main voltage on AN1 will modify the commanded pulse width to maintain the available power in coag and bipolar independent of mains variations. The modified ONTIME, $T_{on}$, is calculated by the microprocessor according to the following arithmetic algorithm: $T_{on} = T_{on}(\text{nominal}) \times (256 - \text{VSENSE})/128$, where $T_{on}$ is the actual ONTIME in either the coagulation or bipolar modes, $T_{on}$(nominal) is the ONTIME at the nominal line voltage, which is predetermined by the setting of the coagulation or bipolar, dial, and VSENSE is the number which the microprocessor reads as the AN1 input signal. Potentiometer 287 (FIG. 11) is set so that VSENSE is equal to 128 when the line voltage is nominal. The microprocessor 50 determines the number for $T_{on}$(nominal) by reading the coagulation or bipolar dial setting (the signal AN0) and dividing by 4, that is, $T_{on}$(nominal)=the dial reading/4. The ONTIME calculated is output by the microprocessor at port 1 and decoded by gate waveform regstor 80 to provide an ONTIME to the gate waveform counter. The operation of the Gate Waveform Generator/Driver to utilize this ONTIME signal will be discussed below. Should a hardware failure cause AN1 to drop to an excessively low value, the microprocessor 50 will declare a failure, as above, rather than trying to command an excessively wide pulse width.

Since there is a fixed relationship at the nominal mains voltage between the coag or bipolar pulse width and the displayed power, the trimmer 287 is provided on the divider feeding AN1 to compensate for unit-to-unit variations in the gain of the power amplifier to set the measured output power in coag to that displayed on the front panel. This effect is achieved by causing the microprocessor 50 to interpret the mains voltage as slightly high or low, thereby causing the voltage compensation routine to make the commanded pulse width slightly narrower or wider than normal.

There is no independent calibration for bipolar power because, unless there is a failure in the bipolar output circuit, output power in that mode will be within specified accuracy if coag is properly calibrated.

The signal POR is generated by the RC delay circuit of FIG. 12 and goes true for about 250 ms after power is applied to the unit. Connection of this signal to the microprocessor 50 RST pin causes the program to start running at the initialization routine when RST goes false. The signal /POR generated by inverter 304 is used to clear the lamp/relay register 61 turning off all indicator lamps and relays.

The power-on reset circuit is designed to ensure orderly power up. When the power is off, the +5-volt supply is essentially at zero volts. This causes capacitor 297 to be essentially discharged through diode 299 and resistor 298. When AC power is switched on, the +5-volt supply will rapidly rise to its regulated voltage causing the microprocessor 50 and other logic to begin operating. The voltage on capacitor 297 rises at a much slower rate so that after the +5 voltge supply has risen to normal levels, the input to NAND gate 300 sees a logic zero. This forces POR true resulting in: (a) an RST condition being forced to the microprocessor 50, and (b) the clearing of the relay enable flag and clearing the lamp and relay register, turning off all relays and display lamps except for the dim patient plate lamp and the MACHINE ERROR indicators. This condition will persist for about 250 ms, when the voltage on capacitor 297 rises above the threshold of gate 300, causing POR to go false until power is removed. The ¼ second POR period is long enough to ensure that the microprocessor 50 crystal starts, that it will begin program execution at the correct point and that all of its I/O port pins are allowed to go high. This time also lets the watchdog timer recover to a reset condition and the waveform generator to fall into its normal states.

The microprocessor 50 is programmed to detect many of its possible internal defects. The detection process necessarily depends upon proper execution of at least a portion of the machine's program. There are a number of possible failures in the microprocessor 50 which evade detection internally, so some external means must be provided to detect them.

The watchdog timer 65 (WDT) checks the program execution time, which is a reliable indicator of the central processor's health. This method requires that the processor execute certain portions of its program within defined time limits. The execution time is measured by monitoring special output signals which are generated by the program. If the watchdog timer detects these pulses at improper intervals, it will initiate action to minimize the impact of a processor failure.

The microprocessor 50 is programmed to generate a signal, /WDTSTB, once every time the main program loop is executed. Depending on various internal and external conditions, the main loop requires 23 to 35 ms to execute, so the time between successive WDT strobes will normally fall in that range. If, however, the program gets lost, tied up in an endless loop or takes a "shortcut" due to an internal failure, /WDTSTB will occur too early, too late or never again. Having detected this condition, the WDT will take the following action:

(1) Lock up in a failed state so that any subsequent /WDTSTB cannot restore operation;
(2) Disable the −15VRF power source 44 to the amplifier gate and base drivers thus inhibiting further RF output;
(3) produce an external interrupt at the TO pin of the microprocessor 50; If the microprocessor 50 is healthy enough to respond to this interrupt, it will execute the FATAL routine with an error code -6-;
(4) Illuminate the MACHINE ERROR lamp on the front panel.

The following list of software functions commences at Power-On Reset and must be successfully executed before the main working program can be entered:
(a) Initialize outputs to relays 110 and indicators 72 through 73;
(b) Blank LEDs 71;
(c) Verify that data memory input/output lines function properly and without crosstalk, and that each bit can accept a zero and a one;
(d) Determine if program memory in all locations where the program resides is intact;
(e) Perform watchdog timer 65 calibration loop upon receipt of appropriate footswitch 10 commands on power-up to aid in troubleshooting the pulse-width generating and RF drive disabling hardware;
(f) Bypass power-up amplifier self-test upon receipt of appropriate footswitch 10 commands on power-up to aid in troubleshooting the RF control and output circuitry when the base and collector fuses 165, 168 are removed for testing;
(g) If footswitch 10 commands not received in either (e) or (f) above, then check that the watchdog timer 65 is capable of ending program execution in the event of strobes to the watchdog timer occurring either sooner or later than expected;
(h) Check that RF supply current is within upper bounds for zero, low, medium and high coag power levels, that supply current is within lower bound for high coag power level, and that the watchdog timer 65 reliably disables RF drive (RF supply current decreases when it times-out);
(i) Display 8s in all LEDs 71 and sound all (four) tones for operator vertification, as well as illuminate all status indicators if all of the above tests are passed;
(j) Initialize data memory locations as necessary for the working program;
(k) Update all displays for dial settings on power-up;
(l) Enable RF output relays 110 and pass control to the working program.

Failure of any of the above self-tests will result in the end of program execution and a display of "HLP" on the Cut Power Level LEDs. The Machine Error indicator will be illuminated. A 1 Kz tone will be sounded to alert the operator and an error code will be displayed on the Coag Power Level LEDs to indicate which test failed.

Main program loop is executed continuously, calling the working subroutines and refreshing the watchdog timer circuit on each pass through the loop.

Bipolar, handcontrol, footswitch and patient plate inputs 122 through 126 are monitored for changes. The validity of these input conditions are checked; if more than one command to activate the output is received simultaneously, a multiple alarm flag is set. If any monopolar command is received and the patient plate is not connected, a plate alarm flag will be set. The multiple alarm flag will result in the OPERATOR ERROR indicator being lit. A 962 Hz fixed high volume tone will be sounded. The plate alarm flag will result in the patient PLATE indicator lamp being brightly illuminated. A 705 Hz fixed high volume tone will be sounded. Either error will disable the RF drive and open all output relays 110.

Response to the above input conditions is dependent on the current active mode. If no inputs are active, or if inputs are invalid, power update subroutines related to the bipolar, cut and coag modes are accessed in turn. Only subroutines related to the active mode and accessed otherwise. If there is no command active, the RF drive and all output relays are deactivated.

The Gate Waveform Generator/Driver 33 (see FIG. 14) produces the Gate A and Gate B signals for a time controlled by microprocessor 50 (see above) in the following manner. The microprocessor 50 controls the waveform generator (WFG) via output signals P10 through P17, /WFGSTB and /RFENA (P24). When /RFENA is true (low), the inverted and amplified signal WFGCTR−Q11 appears on the power amplifier gate drive lines, GATEA and GATEB. When /RFENA is false (high) these drive signals are forced to a low voltage condition, halting generation of RF by the power amplifier.

The microprocessor 50 controls the frequency and duty cycle of the gate waveform by formulating an 8-bit control byte on Port 1 and executing the expander instruction to generate /WFGSTB which, when synchronized with the rising edge of the Q1 output of the WFG counter 84 (WFGCTR−Q1), transfers the control byte to the WFG Register 80. The low-order 6 bits of this byte establishes the duration of the FET conduction time, ONTIME, i.e. the width of the +15 V pulse appearing in GATEA and GATEB, to a resultion of 55.55 ns. The two high order bits select the duration of the OFFTIME portion of the drive cycle via the Offtime Decoder 85. At the end of OFFTIME, the decoder reloads the WFGCTR with ONTIME, and a new cycle starts.

The two higher order bits of the 8-bit control byte on Port 1 of microprocessor 50 also control the COAG−Q and BLENED−Q signals. When the Cut Mode is activated Coag−Q and Blend−Q are both made false (low). When the Blend mode is activated Blend−Q is true (high) and COAG−Q is false (low). When either the COAG or Bipolar modes are activated Blend−Q is false and Coag−Q is true (high). Once a mode is set, these signals are stored in Register 80 and remain unchanged until activation of a different mode changes the higher order bits of the Port 1 output of microprocessor 50.

The WFGCTR 84 is a 12-bit synchronous preloadable binary counter formed from three cascaded 4-bit counter ICs 316, 317, and 318 clocked continuously at 18.00 MHz. The count-enable inputs (P and T) are made true for successive stages so that the counter will increment continuously on each rising edge of the 18 MHz clock, until the offtime decoder detects a selected count. At that time, the decoder 85 drives /WFGLD true (low) to the WFGCTR 84 load enable input (LD), causing the counter 84 to assume the state of its preload inputs (ON TIME PRELOAD) on the next clock edge. Since the high order preload bit is always 0, and all valid counts require WFGCTR−Q11 to be true, the Offtime Decoder 85 will take /WFGLD false (high) immediately after loading has taken place thus allowing the WFGCTR 84 to increment upward from the preloaded value.

Figure 19:
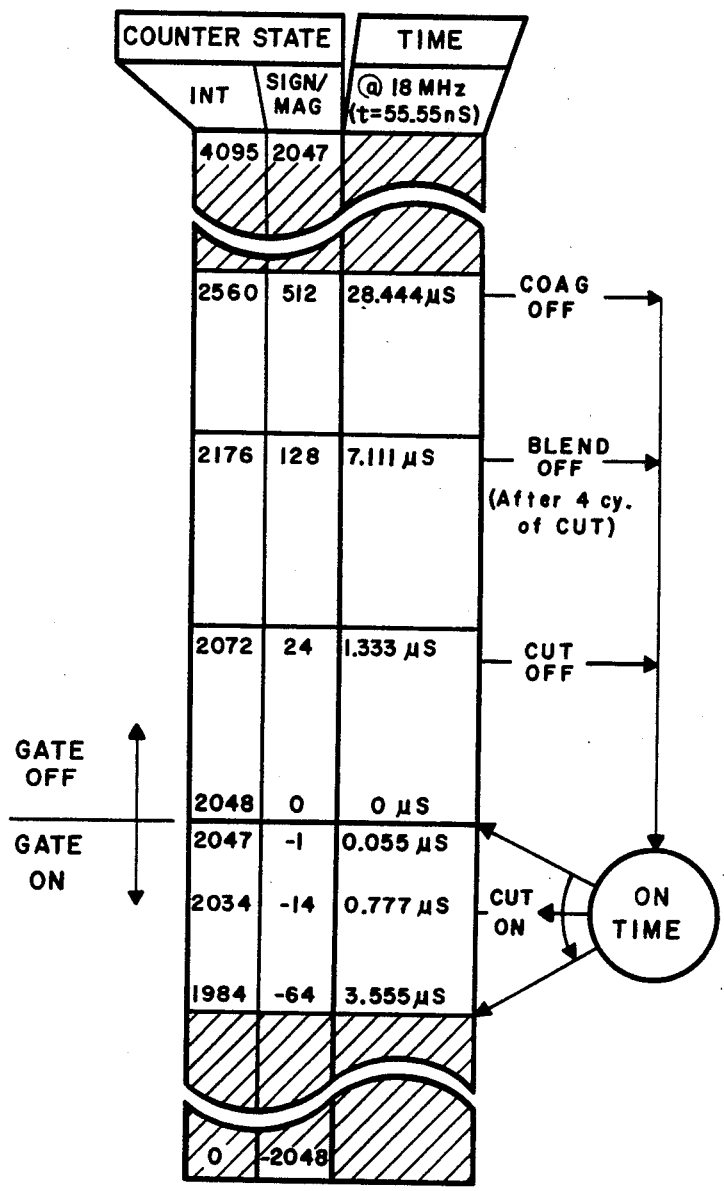
FIG. 19 is a diagram showing the waveform generator counter states at specified times of the counter cycle.

The operation of the WFGCTR 84 cycle may be better understood by referring to FIG. 19 which shows the WFG State/Time Line Diagram.

The Base Voltage Generator/Driver produces the VBASE signal in the following manner. Referring to FIGS. 15 and 16 and working backwards from the circuit output signal, VBASE, the Base Driver is an analog power amplifier powered from +15RF, a +15VDC supply which drops to about +1.2VDC when the Watchdog Timer 65 detects a malfunction (see above). This voltage is low enough to prevent RF output under any combination of hardware failures.

The Driver comprises power transistor 375, one-half of a dual op-amp 97 with a minor loop phase lead feedback capacitor 370 and a major loop resistive feedback network, whose overall DC gain is set by resistors 371 and 365 such that VBASE will be 1.85 time the voltage of the driver input signal, BASELEV.

The MULTIPLEXER selects the source of BASELEV as directed by control signals /RFENA from the microprocessor 50 and COAG−Q from the Gate Waveform Generator (see FIG. 14). When /RFENA is high, BASELEV is forced to less than 0.3 V, reducing VBASE below the 0.6 V necessary to cause base current to flow in the power amplifier 23 and thus disabling RF output. Referring to the schematic, this control is implemented by causing FET 360 to conduct heavily when /RFENA goes high thus pulling BASELEV to ground. Note that this action is redundant to the turning off of gate drive by /RFENA in the Waveform Generator; this redundancy prevents a single point failure from allowing the power amplifier to continue operation when the microprocessor 50 has taken /RFENA high (false).

When /RFENA is low (true), BASELEV will be set to the more positive of either CUTDRV−V or COAGDRV−V via the analog OR gate formed by diodes 352 and 357. When COAG−Q is true as in Coag and Bipolar operation, the voltage divider formed by resistors 93A and 93B is unshorted by inverter 322 (FIG. 14) and open-collector driver 350, allowing COAGDRV−V to rise to a level necessary to set VBASE to the desired +10VDC. This voltage is higher than any which can appear on CUTDRV−V, so it will control BASELEV regardless of the setting of the Cut Power Level control 99.

When COAG−Q is low (false) and /RFENA is low (true), BASELEV will be controlled by CUTDRV−V, which varies from less than +0.5 V to the voltage of CUTDRV−REF (about +5 V) as the Cut Power Level Control 99 is rotated clockwise over its full range. Resistor 383 tailors the linearity of CUTDRV−V versus dial angle to cause the cutting effectiveness versus dial setting to approximate that of older electrosurgical generators with which the O.R. staff may be more familiar. Thus, as the Cut Power Level Control 99 is advanced, VBASE will increase, thereby raising the RF power delivered in Cut mode by the Power Amplifier 23.

As mentioned earlier, CUTREF−V is nominally +5 V, however, its exact voltage is a function of both line voltage and peak power amplifier collector voltage. CUTDRV−REF is generated by the other half of the dual op amp 410. This stage is configured as inverting variable gain summing amplifier 410 working around the +5-volt analog reference, +5REF.

This circuit sums and inverts two analog input signals. One input is a sample of the unregulated +12-volt supply. This sample is produced by the trimmable voltage divider formed by resistors 390, 392, 393, and 91 which is nominally set to produce a CUTDRV−REF voltage of +5.0 V when the AC mains voltage is exactly nominal. This voltage enters the summing junction of op amp 410 via the photo resistor part of optoisolator 400. The resistance of this path decreases from a very high value (several megohms) when the incandescent lamp in optoisolator 400 is dark to a few hundred ohms as the lamp current increases to its full rated value. This resistance adjusts the gain of CUTDRV−REF to variation in +12 V and thus th AC mains voltage. Assuming the lamp is lit brightly, causing a high gain condition, and the mains voltage drops, the sampled +12 V signal will drop below +5REF, causing CUTDRV−REF to rise above +5 V. This results in an increase in VBASE sufficient to overcome the loss of RF output power from the power amplifier 23 caused by a drop in the +120 V supply due to the low AC mains voltage. The opposite action takes place when the mains voltage rises above nominal.

This feedforward regulation has the net effect of holding cut power output relatively constant at a given dial setting as the AC mains voltage varies over the full specific range. Thus the same therapeutic effect can be expected by the O.R. staff at a given dial setting regardless of variations in mains voltage.

The feedforward gain, or the degree to which VBASE is affected by mains voltage, varies directly with the lamp current in optoisolator 400. The lamp current in turn is controlled by CUTSET−V which is directly proportional, from zero to +5 V, to the position of the Cut Power Level Control 99. The result of this is that at cut dial settings below about "5", VBASE will be essentially uneffected by the mains voltage, and at higher settings the effect becomes greater and greater. This corresponds directly with the effect that variations in the unregulated +120VDC supply has on RF output power at different VBASE voltages. At VBASE voltages corresponding to cut control settings up to about "5", there is insufficient base current drawn to cause the Power Amplifier 23 to saturate. Thus the peak to peak voltage on the collector bus 144 and therefore in the RF output transformer will remain relatively constant regardless of the exact voltage delivered by the +120VDC supply. At such low settings, the RF output power will be essentially independent of normal variation of the mains voltage, thus a constant VBASE at a given low dial setting is satisfactory. However, as the cut control setting is advanced above about "5", the power amplifier 23 will saturate during part of the output cycle. When this occurs, the voltage impressed across the RF output transformer 112 or 114 will be nearly equal to the +120VDC supply and will vary accordingly. At even higher dial settings, the portion of the cycle period spent in saturation increases, therefore increasing the influence of the supply voltage over RF output power. The non-linear transfer characteristic of optoisolator 400 closely matches the line voltage versus VBASE versus power output characteristics of the Power Amplifier 23.

A second input to the CUTDRV−REF summing junction 410 is a rectified and filtered sample of the peak positive RF output voltage. This voltage, provided by the output voltage sense circuitry 111, is utilized by the summing junction to limit the voltage at the outputs 22 when the unit is not in Coag. mode. When this signal, VCOLL, reaches about +5.6VDC, diode 415 will conduct, causing CUTDRV−REF to drop, thereby reducing VBASE and the RF power delivered by the power amplifier 23. The purpose of this effect is to limit the open circuit RF output voltage in Cut and Blend and thus the amount of power delivered to high load impedances. The RF output voltage is sampled by a single-turn auxiliary secondary winding 113 on the monopolar output transformer 112. This winding is phased such that its ungrounded end is in phase with the power amplifier collector bus 144 voltage. Capacitor 191 (FIG. 4) is charged to the positive peak of the sampled voltage. The voltage on capacitor 191 is divided by resistors 192 and 193 to roduced VCOLL which is applied to the anode of diode 415. Since the op amp 410 will keep the voltage difference between its + and − input terminals equal, VCOLL will have no effect on VBASE until it becomes at least +5REF plus the forward drop of diode 415. At higher VCOLL voltages, VBASE will drop rapidly thus holding the RF output voltage relatively constant.

This circuit will begin to act in Cut and Blend at a maximum cut dial setting when the RF load resistance exceeds 700 ohms, and will limit the open-circuit output voltage in those modes to less than 2000VP−P. The circuit will reduce CUTDRV−REF to nearly zero when operating in Coag, but diode 357 in the analog OR gate will prevent this from affecting VBASE.

A beneficial side-effect of this circuit is a reduction in AC mains current drain with no RF load to less than ⅓ of that drawn when delivering power to a 400 ohm load.

The Power Amplifier (PA) is configured as a solid-state Hybrid Cascode amplifier for all modes of operation. The schematic for the preferred amplifier is shown in FIG. 3.

FIG. 2 shows the basic Hybrid Cascode amplifier. The bipolar device, 24 is operated in a common-base mode. The base bias voltage, VBASE, is on the order of tens of volts, thereby permitting the use of a low-volage, low resistance FET 25. The amplifier's load, Z1, is supplied by V+ (100 to 140VDC). The FET's gate 28 is driven on and off by a fixed-amplitude, variable frequency and duty-cycle rectangular voltage, VGATE.

In the OFF condition, the VGATE is near ground, turning off the channel so no drain current can flow. Thus no base or emitter current can flow in the bipolar transistor 24. Since V+ is always greater than VBASE, the collector-base junction is reverse-biased, so no collector current will flow and no power is delivered to the load.

Turn-on commences with VGATE rising rapidly to about +15VDC. This results in a large pulse of base current flowing in transistor 24 from Cb (capacitor 135), quickly turning transistor 24 on which will start delivering power to Z1.

After the turn-on transient, FET 25 will be turned on hard and transistor 24 will draw collector current in proportion to its base current, which in turn is controlled by VBASE and resistor 137. At sufficiently high base current, transistor 24 will saturate (collector-base voltage nearly zero), transferring maximum available power to Z1 while transistor 24 and FET 25 dissipate little power due to the low voltage across them.

Turn-off commences with VGATE quickly dropping to nearly 0 V thus shutting off the channel. This effectively disconnects transistor 24's emitter 24A from the circuit. Consequently, collector current flowing at that instance has no alternative but to flow out from the base terminal, charging the base bypass capacitor Cb. This process rapidly depletes the charge stored in the bipolar transistor 24 during turn on, resulting in very fast turn-off (0-500 ns). When transistor 24 is fully turned off, power transfer to Z1 will terminate. The collector voltage may rise to many times the value of V+; however, since the emitter is now disconnected, the collector-base voltage can take on the highest value which that junction will sustain with little chance of second-breakdown.

The base bypass capacitor, Cb, is sized to ensure that it can absorb all of the stored turn-off charge without allowing FET drain 25b voltage to approach its breakdown limit. Further, this charge is now available to charge the base 28 on the next cycle, thereby significantly reducing the net current drain from the VBASE supply.

The saturated operation described above takes place in both Coag and Bipolar operation, including during fulgration, and during high-power (>150 W) Cut. During the latter mode, power increases take place because the dynamics of Z1 allow transistor 24 to saturate over a greater proportion of the conduction cycle as VBASE is increased. Once saturation occurs, excess stored charge accumulates, extending the time required to remove the charge on turn-off and effectively increasing the duty cycle of the amplifier. At lower Cut power settings, VBASE is too low to allow saturation, so transistor 24 will conduct only partially, absorbing some of the power which could otherwise be supplied to Z1. This mode is not as efficient as saturated operation because transistor 24 see simultaneous voltage and current, however, the current at this point is low enough to limit the transistor's dissipation to what can easily be dissipated by the heat sink without excessive junction temperature rise. When VBASE drops to below about 0.6 V, no power will be delivered to the load since this voltage is too low to cause base current to flow.

In Cut, VGATE is a 33% duty cycle, 0 to +15-volt rectangular wave, and VBASE is varied from about 0.3 to +8.5VDC to control output power. The same is true in Blend except that VGATE is further modulated to produce four cycles of normal Cut followed by four cycles of inactivity. In Coag and Bipolar, VBASE is fixed at a level to ensure saturation (about +10 V) while VGATE is a 33 KHz, 0 to 10% duty-cycle rectangular wave. This variation in conduction time controls the amount of energy stored in the inductive part of Z1 every cycle and therefore varies the output power level.

The power amplifier 23 (FIG. 3) consists of two separate Hybrid Cascode sections connected at the collector bus 144. Each section then comprises a single FET such as 146, driving the emitters (E) of three bipolar transistors such as 147, 148, and 149. Each base (B) has its own base current control network which is driven from a common VBASE supply. Each collector (C) and each base (B) is separately fused, allowing a failed part to disconnect itself from the circuit without seriously affecting performance. Failure of either FET 146 or 152 will reduce RF power available by about half, since the working half will continue to operate. Voltage snubbing networks protect VGATE, VBASE and the FET drains (D) from being damaged in the event of any transistor failure, thus limiting the extent or failure propagation.

Each collector is supplied with a diode such as 167, which allows the voltage on the output bus 144 to swing negative with respect to ground, as it does in all modes of operation at sufficiently high power and low external load.

RF output power may be supplied through one of two isolation transformers 112 or 114 (FIG. 4), as selected by the bipolar relay, 115, 184. When deenergized, relay 184, 115 connects the power amplifier collector bus 144 to the monopolar output transformer 112, which is resonated by capacitors 203 and 205 and C3 and damped by resistors 301 and 202. The main secondary of transformer 112 is capacitively coupled by capacitors 118A and 118B and to the patient plate output jack 123 and, via high-voltage reed relays 116 to the user selected monopolar active accessory connectors 124 thru 126. An auxiliary single-turn secondary 113 supplies a replica of the power amplifier collector voltage to the VCOLL circuit which rectifies and peak-detects this signal for use by the control circuitry to limit output voltage in Cut (see above). A leakage cancellation network 212 thru 215 is connected from the patient plate line 216 to ground to help reduce RF leakage due to external patient plate-to-ground capacitance.

When relay 184, 115 is energized, it disconnects transformer 112 and supplies the bipolar output transformer 114, with power from the power amplifier 23. The primary 206 of transformer 114 is resonated by capacitors 203 and 204 and is damped by resistor 201. This transformer is designed to meet the particular requirements of bipolar electrosurgery which is characterized by much lower impedances and permissible voltages than those in monopolar operation. Its secondary 209 is capacitively coupled to the appropriate output connectors.

The feedforward voltage control design described above is a feature of the invention. The design described, permits consistent and reliable therapeutic performance under all operating conditions, with minimal heat dissipation. One particular feature of the feedforward design that is a feature of the invention is the variation of the pulse width (duty cycle) to account for variations in the voltage supply. Another feature is the use of an optoisolator to provide feedforward compensation. As discussed above, the use of the optoisolator permits the power regulation to closely follow the variation in voltage over a very non-linear range.

The microprocessor control of the electrosurgical unit is another feature of the invention. As discussed above the microprocessor permits the signals representing desired characteristics of the system, such as the parameters stored in the program memory for controlling turn on and accurate operation of the system, or the signals produced by the inputs 10 and 14, to be stored and used in controlling the electrosurgical system. In addition to the features mentioned above, the microprocessor has significantly enhanced the safety of the unit as compared to prior electrosurgical unis. At the same time the performance and responsiveness of the system from the users point of view has been increased.

A further feature of the invention is that the principal power consuming components of the power regulating circuitry are also components of the amplifier circuitry. Thus these components perform double duty. As a result, one set of power consuming components, i.e. the power consuming components in the conventional regulated high power supply, are eliminated.

A novel electrosurgical unit that provides a simplified design and at the same time provides efficient and effective regulation of the output power, and which has numerous other features and advantages has been described. While the above description of the invention has been referenced to particular embodiments, as required by the patent law, it is evident that now that the advantages of using a feedforward type circuitry in an electrosurgical unit has been disclosed, those skilled in the art can now make numerous uses of, modifications of, and departures from the specific embodiments described herein without departing from the inventive concepts. Similarly, now that the advantages of using an optoisolator having non-linearity characteristics similar to the amplifier, the advantage of modulating the duty cycle to regulate the power supply and the advantage of using the microprocessor to store a predetermined signal have been shown, those skilled in the art can now substitute many other equivalents of these components. Clearly, those skilled in the art can also substitute many equivalent electronic parts for the particular electronic parts used in the particular circuitry. Further, the design might be simplified as in the case when a more compact unit might be desired, or it might be expanded upon, with other features than those described being added. Likewise the design may be included with other designs and/or functions. Consequently, the invention is to be construed as embracing each and every novel element and novel combination of elements within the appended claims.

What I claim is:

1. An electrosurgical unit comprising:
a. a power source;
b. feedforward means responsive to voltage fluctuations at said power source for producing a regulation signal, said feedforward means including an optoisolator;
c. amplifier means responsive to said regulation signal for producing an electrosurgical output signal that is substatially independent of the voltage fluctuations of said power source;
d. means for controlling the power level of said amplifier means and the lamp brightness of said optoisolator; and
e. means connecting the photo-resistor of said optoisolator to said power source and also to said amplifier means.

2. An electrosurgical unit as in claim 1 wherein said feedforward means includes a microprocessor.

3. An electrosurgical unit as in claim 1 wherein said amplifier means includes a means for pulse modulating said electrosurgical output signal, and said feedforward means comprises a means for producing a signal for regulating the duty cycle of said modulated output.

4. An electrosurgical unit as in claim 1 wherein said feedforward means comprises:
a means for storing a predetermined signal representative of a desired voltage; and
means responsive to the voltage fluctuations of said source and to said predetermined signal for producing said regulation signal.

5. An electrosurgical unit comprising:
a. a power source; and
b. an amplifier means electrically connected to said power source for producing an electrosurgical output signal, said amplifier means including a means for manually controlling the power level of the amplifier, and further including a means for regulating the output signal having a means responsive to said means for controlling for adjusting for nonlinearities in said amplifier, said means for adjusting including an optoisolator connected to said power source and said amplifier means.

* * * * *